US011135156B2

(12) United States Patent
Topsoe et al.

(10) Patent No.: US 11,135,156 B2
(45) Date of Patent: Oct. 5, 2021

(54) PHARMACEUTICAL TABLET FOR USE IN ADMINISTERING ONE OR MORE PHARMACEUTICALLY ACTIVE INGREDIENTS

(71) Applicant: FERTIN PHARMA A/S, Vejle (DK)

(72) Inventors: Martin Topsoe, Vejle (DK); Kirsten Lund, Juelsminde (DK)

(73) Assignee: FERTIN PHARMA A/S, Vejle (DK)

( * ) Notice: Subject to any disclaimer, the term of this patent is extended or adjusted under 35 U.S.C. 154(b) by 105 days.

(21) Appl. No.: 15/602,968

(22) Filed: May 23, 2017

(65) Prior Publication Data

US 2017/0367975 A1  Dec. 28, 2017

Related U.S. Application Data

(63) Continuation of application No. 15/136,553, filed on Apr. 22, 2016, now abandoned, which is a continuation of application No. 11/664,985, filed as application No. PCT/DK2005/000650 on Oct. 10, 2005, now abandoned.

(30) Foreign Application Priority Data

Oct. 8, 2004   (WO) ............... PCT/DK2004/000691
May 20, 2005   (WO) ............... PCT/DK2005/000335

(51) Int. Cl.
| *A61K 9/00* | (2006.01) |
| *A23G 3/36* | (2006.01) |
| *A23G 4/20* | (2006.01) |
| *A23G 4/08* | (2006.01) |
| *A23G 4/18* | (2006.01) |
| *A24B 13/00* | (2006.01) |
| *A61K 9/68* | (2006.01) |
| *A61K 9/20* | (2006.01) |
| *A23L 33/10* | (2016.01) |
| *A23G 3/42* | (2006.01) |
| *A24B 15/10* | (2006.01) |
| *A23G 4/10* | (2006.01) |
| *A61K 31/465* | (2006.01) |

(52) U.S. Cl.
CPC ............ *A61K 9/0056* (2013.01); *A23G 3/36* (2013.01); *A23G 3/42* (2013.01); *A23G 4/08* (2013.01); *A23G 4/10* (2013.01); *A23G 4/18* (2013.01); *A23G 4/20* (2013.01); *A23L 33/10* (2016.08); *A24B 13/00* (2013.01); *A24B 15/10* (2013.01); *A61K 9/0058* (2013.01); *A61K 9/2027* (2013.01); *A61K 31/465* (2013.01); *A23V 2002/00* (2013.01)

(58) Field of Classification Search
None
See application file for complete search history.

(56) References Cited

U.S. PATENT DOCUMENTS

| 2,700,012 A | 1/1955 | Merckel et al. |
| 2,915,024 A | 12/1959 | Kruger et al. |
| 3,440,060 A | 4/1969 | Rife et al. |
| 3,470,831 A | 10/1969 | Von Drachenfels |
| 3,877,468 A | 4/1975 | Lichtneckert et al. |
| 4,032,667 A | 6/1977 | Kreuter et al. |
| 4,127,677 A | 11/1978 | Fronczkowzki et al. |
| 4,224,345 A | 9/1980 | Tezuka et al. |
| 4,238,510 A | 12/1980 | Cherukuri et al. |
| 4,272,548 A * | 6/1981 | Gatzen ............... A61K 31/23 514/547 |
| 4,317,837 A | 3/1982 | Kehoe et al. |
| 4,352,822 A | 10/1982 | Cherukuri et al. |
| 4,352,824 A | 10/1982 | Puglia et al. |
| 4,357,359 A | 11/1982 | Cloud et al. |
| 4,385,071 A | 5/1983 | Yakimischak |
| 4,415,596 A | 11/1983 | Andersen et al. |
| 4,450,179 A | 5/1984 | Vink et al. |
| 4,468,185 A | 8/1984 | Jansen |
| 4,486,452 A | 12/1984 | Cloud et al. |
| 4,518,615 A | 5/1985 | Cherukuri et al. |
| 4,555,407 A | 11/1985 | Kramer et al. |

(Continued)

FOREIGN PATENT DOCUMENTS

| EP | 0242325 A2 | 10/1987 |
| EP | 0271445 A2 | 6/1988 |

(Continued)

OTHER PUBLICATIONS

Cantore, G., "Oral Glycerol for the Reduction of Intracranial Pressure", J. Neurosurgery, 1964, pp. 278-283. (Year: 1964).*
Sigma-Aldrich, "General Properties of Casein",accessed from: https://www.sigmaaldrich.com/life-science/metabolomics/enzyme-explorer/enzyme-reagents/casein.printerview.html, accessed on Aug. 22, 2018, pp. 1—(Year: 2018).*
KR20010078976A Translation, accessed from: "https://translate.google.com/translate?hl=en&sl=ko&tl=en&u=htthttps%3A%2F%2Fpatents.google.com%2Fpatent%2FKR20010078976A%2Fko%3Foq%3DKR20010078976" accessed on Dec. 18, 2019, pp. 1-36 (Year: 2019).*

(Continued)

*Primary Examiner* — Michael G. Hartley
*Assistant Examiner* — Lance W Rider

(57) ABSTRACT

A pharmaceutical tablet for use in administering one or more pharmaceutically active ingredients, comprising a polymer system, the one or more pharmaceutically active ingredients, a flavor, and a sweetener, wherein at least 20% by weight of the pharmaceutical tablet comprises substantially non-elastomeric polymer and less than 5% by weight of the pharmaceutical tablet comprises one or a combination of elastomeric polymers, and wherein the pharmaceutical tablet comprises at least 70% by weight of said polymer system comprising polyvinyl acetate (PVA) and less than 10% by weight of said polymer system comprising polymer having a molecular weight (Mw) greater than 50,000 g/mol.

11 Claims, 3 Drawing Sheets

(56) References Cited

U.S. PATENT DOCUMENTS

| | | | |
|---|---|---|---|
| 4,624,269 A | 11/1986 | Story et al. | |
| 4,721,620 A | 1/1988 | Cherukuri et al. | |
| 4,794,003 A | 12/1988 | Cherukuri et al. | |
| 4,889,726 A | 12/1989 | Dave et al. | |
| 4,895,732 A | 1/1990 | Suwa et al. | |
| 4,929,447 A | 5/1990 | Yang | |
| 4,933,189 A | 6/1990 | Cherukuri et al. | |
| 4,968,511 A | 11/1990 | D'Amelia et al. | |
| 5,002,791 A | 3/1991 | Knebl | |
| 5,023,093 A * | 6/1991 | Cherukuri | A23G 4/02 426/103 |
| 5,035,905 A | 7/1991 | Knebl | |
| 5,110,608 A | 5/1992 | Cherukuri et al. | |
| 5,116,626 A * | 5/1992 | Synosky | A23G 4/08 426/3 |
| 5,125,819 A | 6/1992 | Hager et al. | |
| 5,173,317 A | 12/1992 | Hartmann et al. | |
| 5,279,846 A | 1/1994 | Okumura | |
| 5,358,729 A | 5/1994 | Onkuma et al. | |
| 5,480,664 A | 1/1996 | Ferrero | |
| 5,487,902 A | 1/1996 | Andersen et al. | |
| 5,505,982 A | 4/1996 | Krawczyk et al. | |
| 5,601,858 A * | 2/1997 | Mansukhani | A23G 4/00 426/3 |
| 5,741,505 A | 4/1998 | Beyer et al. | |
| 6,143,345 A | 11/2000 | Gonze et al. | |
| 6,200,608 B1 * | 3/2001 | Gmunder | A23G 4/00 426/3 |
| 6,251,454 B1 | 6/2001 | Layfield | |
| 6,280,780 B1 | 8/2001 | Degady et al. | |
| 6,344,222 B1 | 2/2002 | Cherukuri et al. | |
| 6,531,114 B1 | 3/2003 | Gmunder et al. | |
| 6,558,727 B2 | 5/2003 | Degady et al. | |
| 6,599,542 B1 | 7/2003 | Abdel-Malik et al. | |
| 6,627,233 B1 | 9/2003 | Wolf et al. | |
| 6,703,000 B2 | 3/2004 | Ning et al. | |
| 6,730,344 B1 | 5/2004 | Sanders et al. | |
| 6,759,079 B2 | 7/2004 | Kung et al. | |
| 6,805,890 B2 | 10/2004 | Wu et al. | |
| 6,838,098 B2 | 1/2005 | Bunkers et al. | |
| 7,056,542 B1 * | 6/2006 | Bridger | A23G 4/064 426/3 |
| 2001/0002998 A1 | 6/2001 | Ream et al. | |
| 2002/0058102 A1 | 5/2002 | Makela et al. | |
| 2002/0098264 A1 * | 7/2002 | Cherukuri | A23G 4/12 426/3 |
| 2002/0192330 A1 | 12/2002 | Bunkers et al. | |
| 2003/0082291 A1 | 5/2003 | Davila et al. | |
| 2004/0013776 A1 | 1/2004 | Whitehouse et al. | |
| 2004/0115305 A1 | 6/2004 | Andersen et al. | |
| 2004/0142066 A1 | 7/2004 | Andersen et al. | |
| 2004/0180111 A1 | 9/2004 | Andersen et al. | |
| 2006/0099300 A1 | 5/2006 | Andersen et al. | |
| 2009/0311368 A1 | 12/2009 | Wittorff | |

FOREIGN PATENT DOCUMENTS

| | | | |
|---|---|---|---|
| EP | 0273009 A2 | 6/1988 | |
| EP | 0372695 A1 | 6/1990 | |
| EP | 0727146 A2 | 8/1996 | |
| EP | 1796482 A1 | 6/2007 | |
| EP | 1796483 A1 | 6/2007 | |
| FR | 2796813 A1 | 2/2001 | |
| GB | 711187 A | 6/1954 | |
| GB | 2018668 A | 10/1979 | |
| JP | 4823974 A | 3/1973 | |
| JP | 4819950 A | 6/1973 | |
| JP | 56078560 A | 6/1981 | |
| JP | 5712958 A | 1/1982 | |
| JP | 57198050 A | 12/1982 | |
| JP | 26005888 B | 12/1984 | |
| JP | 60083539 A | 5/1985 | |
| JP | 62236447 A | 10/1987 | |
| JP | 63214147 A | 9/1988 | |
| JP | 63245638 A | 10/1988 | |
| JP | 2222650 A | 9/1990 | |
| JP | 2004518447 A | 6/2004 | |
| KR | 20010078976 A * | 8/2001 | |
| RU | 2176885 C2 | 12/2001 | |
| WO | 9620609 A1 | 7/1996 | |
| WO | 0025598 A1 | 11/1998 | |
| WO | 0040101 A1 | 7/2000 | |
| WO | 0002460 A1 | 1/2001 | |
| WO | 0110238 A1 | 2/2001 | |
| WO | WO-0149124 A1 * | 7/2001 | ............... A23G 4/06 |
| WO | 0156397 A1 | 8/2001 | |
| WO | 0215708 A2 | 2/2002 | |
| WO | 0219835 A1 | 3/2002 | |
| WO | 02076229 A1 | 10/2002 | |
| WO | 02076230 A1 | 10/2002 | |
| WO | 02076231 A1 | 10/2002 | |
| WO | 02102357 A1 | 12/2002 | |
| WO | 03059079 A1 | 7/2003 | |
| WO | 03105594 A1 | 12/2003 | |
| WO | 2004004478 A1 | 1/2004 | |
| WO | 2004004479 A1 | 1/2004 | |
| WO | 2004004480 A1 | 1/2004 | |
| WO | 2004028265 A1 | 4/2004 | |
| WO | 2004028267 A1 | 4/2004 | |
| WO | 2004082392 A2 | 9/2004 | |
| WO | 2005016021 A1 | 2/2005 | |
| WO | 2005074701 A1 | 8/2005 | |
| WO | 2006079338 A1 | 8/2006 | |

OTHER PUBLICATIONS

Tablet Definition, "Tablet (Pharmacy)", accessed from: https://en.wikipedia.org/wiki/Tablet_(pharmacy); accessed on Dec. 18, 2019, pp. 1-10 (Year: 2019).*

Hunter, et aL; "Calcium Channel Blockers 1: A Review of Their Mechanisms of Action", Pharmacy International (Nov. 1985) pp. 267-271.

Candy Formulations, Moscow (1970) p. 65.

Minifie, BW., "Chocolate, Cocoa and Confectionery"; Third Ed., Van Nostrand Reinhold (1989).

Food and Drug Administration, CFR, Title 21, Sec. 172.615 (Apr. 1, 2007) pp. 66-68.

Beckett; "Industrial Chocolate Manufacture and Use"; 3rd Ed., Blackwell Publishing Ltd. (1999).

Martindale, The Extra Pharmacopoeia, 28th Ed., Reynolds, James E.F., Editor, The Pharmaceutical Press, London (1982).

Odian, G., "Principles of Polymerization"; Third Ed., John Wiley & Sons, Inc. New York, (1991) p. 17.

Manly, et al.; "Substances Capable of Decreasing the Acid Solubility of Tooth Enamel", J. Dent. Res., vol. 28, No. 2, (1949) pp. 160-171.

Fryer, P, et al., The Materials of Science of Chocolate, MRS Bulletin (Dec. 2000).

Definition of Derivative from Merriam Webster online dictionary, downloaded Jun. 26, 2017 from https://www.merriamwebster.com/dictionary/derivative.

PVAc and Tg Retrieved Jul. 19, 2013. The Webpage updated Jul. 11, 2000.

Green, Jordan R. et al.; Development of Chewing in Children from 12 to 48 Months: Longitudinal Study of EMG Patterns; Journal of Neurophysiology; May 1, 1997; vol. 77; No. 5; pp. 2704-2716.

Fiedler, H.P., Lexikon der Hilfstoffe fur Pharmacie, Kosmetik und Angrenzende Gebiete (1981) pp. 63-64.

European Patent Office; Communication of a Notice of Opposition; Application No. 04762910.0-1221/1796482; Reference P04116WO/EP; dated Apr. 19, 2012.

European Patent Office; International Preliminary Report on Patentability for International Application No. PCT/DK2004/000691; Boddaert, Peter; dated Jan. 12, 2007.

European Patent Office; International Preliminary Report on Patentability for International Application No. PCT/DK2005/000335; Baharlou, Simin; dated Apr. 11, 2007.

European Patent Office; International Search Report for International Application PCT/DK2004/000691; Boddaert, P; dated Jun. 13, 2005.

(56) References Cited

OTHER PUBLICATIONS

European Patent Office; International Search Report for International Application PCT/DK2005/000335; Boddaert, P; dated Sep. 5, 2005.
European Patent Office; International Search Report for International Application PCT/DK2005/000650; Boddaert, P; dated Feb. 1, 2006.
European Patent Office; Written Opinion for International Application No. PCT/DK2004/000691; Boddaert, P; dated Jun. 30, 2005.
European Patent Office; Written Opinion for International Application No. PCT/DK2005/000335; Boddaert, P; dated Sep. 15, 2005.
U.S. Code of Federal Regulations, Title 21, Sections 182.8013-182.8997; retrieved Oct. 24, 2017.
Notification of Reason for Refusal for Application 2007-535017; dated Dec. 22, 2011.
Official Action for Application No. 2007117135; Received May 14, 2008.
Product brochure for Nicorette gum, downloaded Apr. 3, 2018 from http://www.nicorette.com/products/nicorette-gum.html#flavor (Year: 2018).
Official Action for U.S. Appl. No. 15/411,205 (related application); Received Dec. 31, 2018 (18 pages).

* cited by examiner

PHARMACEUTICAL TABLET FOR USE IN ADMINISTERING ONE OR MORE PHARMACEUTICALLY ACTIVE INGREDIENTS

TECHNICAL FIELD

The invention relates to a tablet comprising a polymer system, flavor and sweetener.

BACKGROUND

A group of conventional confectionery products including tablet-formed substances and/or chewable substances, which may be gradually dissolved or chewed and digested, such as candy, jelly, wine gum, liquorice, toffee, etc. This group of confectionery products generally benefits from a large variety of applicable textures, as indicated by the above-mentioned different products.

A problem related to this group of confectionery products, such as e.g. liquorice, toffee, etc, is that these products are consumed relatively fast, so that the consumer repeatedly needs to reload. This may lead to over-consuming, which may be undesirable due to a large intake of calories. In recent years, much attention has been paid to this problem. However, too large calorie-intake due to large consumption of confectionery products seems to be an increasing problem in some countries.

SUMMARY

The present invention relates to a confectionery product comprising a polymer system, flavor and sweetener, wherein at least 20% by weight of said confectionery product comprises substantially non-elastomeric polymer and less than about 5% by weight of said confectionery product comprising one or a combination of elastomeric polymers and wherein said confectionery product is characterized by having a tan (delta) above 1 measured at a frequency of about 1 Hz. and wherein the tan (delta) is defined as (loss modulus G"/storage modulus G').

According to a preferred embodiment of the invention, the confectionery product has a tan (delta) above 1 measured at a frequency of about 0.1 to 10 Hz, i.e. over a relatively broad oscillation frequency.

According to the present invention, a new confectionery product has been obtained having texture properties emulating toffee but comprising a part, which is retained in the mouth during chewing. This confectionery product, according to the invention, is referred to as 'toffee gum'. The toffee gum, according to the invention, has toffee-like properties, but it is not completely swallowed during use. The toffee-like properties may be maintained for a relatively long time, e.g. 10-20 minutes, compared to chewing of a conventional toffee, which is usually swallowed during a shorter period of time.

Basically, the part of the toffee gum being retained in the mouth is substantially formed by the polymer system and parts of further ingredients being retained in the polymer system. Furthermore, according to the present invention, the polymer system, which comprises one or several polymers, is essential in providing the desired toffee-like properties for a prolonged time compared to conventional toffee, caramel, liquorice, wine gum, etc. According to the invention, it is required in obtaining these effects that the polymer system constitutes at least 10% by weight of the toffee gum product.

Thus, the prolonged texture compared to conventional toffee is obtained by way of the polymer system, as the polymers are not ingested during chewing but rather forming part of a toffee-emulating polymer structure, which may be chewed in the same way as a chewing gum. The polymer system may be compared in function to the gum base of a chewing gum, but with significant textural differences.

According to the invention, sweetener, flavor and/or chocolate may be added to the toffee gum as taste providing components, which are substantially swallowed during use of the toffee gum product. Dependent on the affinity for the polymers, specific ingredients may be retained in the toffee gum for shorter or longer times during chewing of the product. Specific desired taste profiles may be obtained by adjusting types and amounts of flavors and sweeteners.

According to an embodiment of the invention, a part of a toffee may be substituted by a polymer system. Thus the toffee texture may be provided by the polymer system and as it is not consumed during use, the texture may be maintained beyond a usual period of time of chewing a toffee. A correspondingly prolonged taste may be obtained due to the fact that some of the taste-providing substances are incorporated into the polymer system, both by initial mixing during manufacturing and/or by mixing occurring during the chewing-process performed by a consumer. Further ways of regulating the length of the taste sensation include incorporation of emulsifiers in the toffee gum and choosing the taste-providing substances in view of their affinity for the polymer system.

Furthermore, according to an embodiment of the invention, the application of the significant amount of polyvinyl acetate in the polymer system makes it possible to obtain an improved release of ingredients such as flavors, sweeteners, and active ingredients.

Herein, the polymer system is used as a term covering the polymers applied in the toffee gum confectionery product according to the invention. The polymer system may comprise one or more types of polymers, typically synthetic.

According to a preferred embodiment of the invention, a toffee gum may be a suitable substitute for conventional toffee or caramel. Toffee gum as a substitute for toffee, caramel, and further soft candies such as liquorice has the advantage of being a low-calorie substitute, which moreover provides prolonged taste sensation.

A way of characterizing the texture of the toffee gum is to measure the rheological properties, which involves the storage modulus G' and the loss modulus G" and the relation between the two. The term storage modulus G' may also be regarded as the elastic modulus, while the term loss modulus G" may be regarded as the viscous modulus. The ratio of G" to G', that is G"/G' or tan (delta), is a measure of the relative importance of the viscous to elastic contributions for a material at a given frequency, and may be evaluated at a given oscillation torque and a given temperature.

Measurements referred to in this application were carried out by an AR 1000 rheometer from TA Instruments and at an oscillation torque of 10 µN·m and 37° C.

The weight reference to the confectionery product refers to the final confectionery product excluding coatings, fillings and hard candy elements attached to the product.

In an embodiment of the invention, said confectionery product is characterized by having a tan (delta) in the range of 1 to 10 measured at a frequency of 0.1 to 10 Hz.

In an embodiment of the invention, said tan (delta) is in the range of 1 to 5 measured at a frequency of 0.1 to 10 Hz.

In an embodiment of the invention, said storage modulus G' is lower than about 40,000 Pa, preferably lower than about 30,000 Pa as measured at a frequency of about 1 Hz.

In an embodiment of the invention, said storage modulus G' decreases during at least a part of a chewing process.

In an embodiment of the invention, said storage modulus G' decreases in the chewing process during the first 1 to 3 minutes.

In an embodiment of the invention, said loss modulus G" is higher than about 10,000 Pa as measured at a frequency of about 1 Hz.

In an embodiment of the invention, said loss modulus G" decreases during at least a part of the chewing process.

In an embodiment of the invention, said loss modulus G" decreases in the chewing process during the first 1 to 3 minutes.

In an embodiment of the invention, said chewing process involves a chewing frequency at about 1 Hz.

In an embodiment of the invention, said storage modulus G' and said loss modulus G" are measured at an oscillation torque of about 8 to 12 μN·m.

In an embodiment of the invention, said storage modulus G' and said loss modulus G" are measured by AR 1000 rheometer from TA Instruments and at a temperature of 37° C.

In an embodiment of the invention, said confectionery product is characterized by having a said loss modulus G" decreasing over time.

In an embodiment of the invention, said confectionery product is characterized by, within the first 3 minutes of the chewing, having a said storage modulus G lower than that of a conventional chewing gum as measured at a chewing frequency of 0.1 to 1 Hz.

In an embodiment of the invention, said confectionery product is characterized by, within the first 3 minutes of the chewing, having a said loss modulus G" lower than that of a conventional chewing gum as measured at a chewing frequency of 0.1 Hz.

In an embodiment of the invention, said loss modulus G" and said storage modulus G' are both lower than about 10,000 Pa as measured at a frequency of about 0.1 Hz.

In an embodiment of the invention, at least about 70% by weight of said polymer system comprising substantially non-elastomeric polymer and less than about 15% by weight of said polymer system comprising one or a combination of elastomeric polymers.

In an embodiment of the invention, at least 30% by weight of said confectionery product comprises substantially non-elastomeric polymer and less than about 5% by weight of said confectionery product comprising elastomeric polymers.

In an embodiment of the invention, said elastomeric polymers include styrene butadiene rubber (SBR), poly isobutylene (PIB), isobutylene-isoprene rubber (IIR), polyisoprene, natural rubber and any combination thereof.

According to an embodiment of the invention, it has been found that it is a key feature of the toffee gum that it comprises a polymer system of which the main part is composed of substantially non-elastomeric polymers and in particular the above-mentioned. It has also been determined, that the rheological properties may be tuned by adjusting the amount of the above-mentioned polymers.

In an embodiment of the invention, said confectionery product comprises less than 3% by weight of said elastomeric polymers.

In an embodiment of the invention, said confectionery product comprises less than 2% by weight of said elastomeric polymers.

In an embodiment of the invention, said confectionery product comprises less than 1% by weight of said elastomeric polymers.

In an embodiment of the invention, said polymer system comprises at least one substantially non-elastomeric polymer in an amount in the range of 70% to 100%, preferably 80% to 100% by weight of said polymer system.

According to an embodiment of the invention, it has been found that it is a key feature of the toffee gum that it comprises a polymer system of which the main part is composed of substantially non-elastomeric polymers.

Polyvinyl acetates of molecular weight in the range of 1,000 to 100,000 g/mol and a glass transition temperature in the range of 18 to 50° C. may show very desirable non-elastomeric properties and are according to the invention very important for obtaining the toffee-like consistency of the toffee gum.

In an embodiment of the invention, said polymer system is substantially formed by at least one substantially non-elastomeric polymer.

In an embodiment of the invention, said confectionery product is substantially free of said elastomeric polymers.

According to an embodiment of the invention, the amount of elastomer should preferably be as low as possible to obtain the desired toffee texture. According to a preferred embodiment of the invention, conventional elastomer should be substantially avoided in the final confectionery product.

In an embodiment of the invention, said polymer system comprises less than 4% by weight of polymers having a molecular weight (Mw) of from about 50,000 to 99,999 g/mol.

In an embodiment of the invention, said polymer system comprises less than 2% by weight of polymers having a molecular weight (Mw) of from about 100,000 to 199,999 g/mol.

In an embodiment of the invention, said polymer system comprises less than 1% by weight of polymers having a molecular weight (Mw) of from about 200,000 to 399,999 g/mol.

In an embodiment of the invention, said polymer system comprises less than 0.5% by weight of polymers having a molecular weight (Mw) of from about 399,000 to 800,000 g/mol.

According to an embodiment of the invention, high-molecular weight polymers, such as conventional elastomers or high-molecular weight polyvinyl acetate, should be kept low in concentration to obtain the desired texture.

Only a small amount of elastomeric polymers can be applied, without spoiling the desired texture of the toffee gum. They may be used for adjusting the texture, and may contribute with more robustness, but preferably elastomers are avoided.

It is crucial for obtaining the desired toffee texture that the amount of elastomeric polymer is kept low. Otherwise, the toffee gum is in danger of acquiring more chewing gum-like textural properties, which are undesired in the toffee gum of the invention.

Evidently, insignificant amounts of other polymers may be acceptable within the scope of the invention without compromising the principles of the invention, namely that the PVA alone provide a toffee-like texture.

In an embodiment of the invention, said confectionery product comprises sweetener in an amount of 2% to 80% by weight of the confectionery product.

Sweeteners, and in particular bulk sweeteners may provide or result in a significant part of the desired toffee-like structure in order to avoid that plasticity of the polymer system dominates the final product with respect to both texture and release.

In an embodiment of the invention, said confectionery product comprises sweetener in an amount of 10% to 75% by weight of the confectionery product.

In an embodiment of the invention, said confectionery product comprises sweetener in an amount of 20% to 70% by weight of the confectionery product.

In an embodiment of the invention, said confectionery product comprises bulk sweetener in an amount of 2% to 80% by weight of the confectionery product.

In an embodiment of the invention, said confectionery product comprises bulk sweetener in an amount of 10% to 75% by weight of the confectionery product.

In an embodiment of the invention, said confectionery product comprises bulk sweetener in an amount of 20% to 70% by weight of the confectionery product.

In an embodiment of the invention, said sweeteners comprises sugar.

In an embodiment of the invention, said sweeteners comprise bulk sweeteners.

According to a preferred embodiment of the invention, artificial sweeteners may advantageously be applied in the toffee-gum-like confectionery product.

In an embodiment of the invention, said artificial sweetener is selected from the group consisting of sorbitol, mannitol, maltitol, xylitol, erythritol, lactitol, isomalt, derivatives of isomalt, or any combination thereof.

Accordingly, any other hydrogenated derivates of mono-, di-, or polysaccharides may be applied in the toffee gum of the invention. Furthermore, it is within the scope of the invention to apply sugar-sweeteners and artificial sweeteners in the same toffee gum composition.

In an embodiment of the invention, said artificial sweetener is a high-intensity artificial sweetener selected from the group consisting of aspartame, salts of acesulfame, alitame, neotame, twinsweet, saccharin and its salts, cyclamic acid and its salts, glycyrrhizin, dihydrochalcones, thaumatin, monellin, stevioside, sucralose, or any combination thereof.

In an embodiment of the inventions the confectionery product comprises less than 30% by weight of filler.

In an embodiment of the invention, said confectionery product comprises filler in the amount of 1% to 30% by weight.

In an embodiment of the invention, the confectionery product comprises filler in the amount of 2% and 15% by weight.

In an embodiment of the invention, said non-elastomeric polymers comprises PVA.

According to an embodiment of the invention, polyvinyl acetate may generally be referred to as non-elastomeric and as having resinous characteristics.

Such properties of the main part of the polymers are essential in order to obtain the desired consistency. Application of elastomers (elastomeric polymers) in too large amounts have been found to spoil the desired consistency—and make the product texture more chewing gum-like, which is far from the desired toffee-like consistency.

Surprisingly, it has been found, according to the invention, that polyvinyl acetate (PVAc) has exactly such properties essential for obtaining a polymer system providing the toffee gum product with toffee-like texture. Accordingly, it has been found that by adding polyvinyl acetate in significant amounts, it is possible to imitate the textural properties of toffee and, obtain a toffee gum product having properties resembling or emulating toffee. The significant amount of polyvinyl acetate according to the invention is at least 70%, preferably more, by weight of the polymer system.

In an embodiment of the invention, said non-elastomeric polymers include low-molecular weight PVA, where said low-molecular weight PVA is having a molecular weight (Mw) of less than about 50,000 g/mol.

In an embodiment of the invention, said non-elastomeric polymers comprise a natural or synthetic resin.

Natural resins or synthetic resins may comprise hydrogenated and polymerized gum resins, glycerol esters of hydrogenated and polymerized gum resins, polyterpene resins PVA or other resins.

In an embodiment of the invention, the polymer system comprises at least one low-molecular weight PVA having a molecular weight (Mw) of about 9,000 to 30,000 g/mol, preferably about 13,000 to 21,000 g/mol.

In an embodiment of the invention, the confectionery product comprises at least one low-molecular weight PVA having a molecular weight (Mw) of about 2,000 to 40,000 g/mol in an amount of from about 70 to 99% by weight of the polymer system.

In an embodiment of the invention, said polymer system of said confectionery product comprises at least about 90% by weight of polyvinyl acetate.

In an embodiment of the invention, said polymer system of said confectionery product comprises at least about 95% by weight of polyvinyl acetate.

In an embodiment of the invention, said polymer system of said confectionery product comprises at least about 99% by weight of polyvinyl acetate.

In an embodiment of the invention, said polymer system is substantially formed by polyvinyl acetate(s) alone.

Basically, a polymer system comprising polyvinyl acetate(s) as the sole synthetic polymer is preferred.

According to a preferred embodiment of the invention, the toffee gum is substantially free of natural and synthetic elastomers, which are typically applied within the art of manufacturing chewing gum.

The toffee texture of the polymer-based confectionery product according to the invention is obtained through a substantial amount of polyvinyl acetate and avoiding use of substantial amounts of high-molecular weight polymers, in particular elastomers.

According to a preferred embodiment of the invention, conventional elastomers should be avoided in order to avoid the typical chewing gum-like elastomeric properties, and according to a most preferred embodiment of the invention, the polymers of the product consist of polyvinyl acetate.

Evidently, insignificant amounts of other polymers may be acceptable within the scope of the invention without compromising the principles of the invention, namely that the polyvinyl acetates alone provide a toffee-like texture.

In an embodiment of the invention, said confectionery product is a toffee gum.

According to an embodiment of the invention, the toffee gum confectionery product may be provided with the desired toffee-like texture on the basis of a polymer system, in which all the polymers comprised are substantially non-elastomeric polymers, mainly polyvinyl acetate, and none of them are elastomers.

In an embodiment of the invention, said polymer system substantially comprises polyvinyl acetate (PVA).

In an embodiment of the invention, the polymer system comprises at least one low-molecular weight PVA having a molecular weight (Mw) of about 2,000 to 40,000 g/mol, at least one high-molecular weight PVA having a molecular weight (Mw) of 40,001 to 200,000 g/mol.

In an embodiment of the invention, the confectionery product comprises at least about 70% by weight of said polymer system comprising polyvinyl acetate (PVA) and less than 10% by weight of said polymer system comprises polymer having a molecular weight (Mw) greater than about 50000 g/mol.

In a preferred embodiment of the invention, said confectionery product comprises
a polymer system in an amount of from about 5% to about 99% by weight, flavor in an amount of about 0.001% to about 30% by weight and sweeteners in an amount of about 5% to about 80% by weight.

According to the invention, a toffee-like chewing gum has been obtained. The backbone of the product is a polymer system, basically equivalent in function to the gum base of conventional chewing gum although with significant textural differences.

In an embodiment of the invention, said polymer system comprises plasticizers.

According to an embodiment of the invention, plasticizers are applied for the purpose of obtaining a soft chew feel of the polyvinyl acetate based polymer system. It is noted that the desired plasticization depends heavily on the other ingredients applied in the product. As an example, some aggressive flavors, such as fruit flavors and acids, tend to soften the polymer system significantly compared to e.g. mint oil-based flavors.

Particularly useful plasticizers, according to the present invention, are triacetin, acetylated mono- and di- and triglycerides of short chain fatty acids, acetylated mono- and di- and triglycerides of medium-chain fatty acids, acetylated monoglycerides of long-chain fatty acids, methyl ester of rosin, low-molecular weight PVA.

A preferred plasticizer will in a preferred embodiment have a hydrophilicity corresponding to the applied PVA.

In an embodiment of the invention, said polymer system comprises less than 30% by weight of plasticizers, preferably less than 20% by weight of plasticizers and most preferably less than 10% by weight of plasticizers.

In an embodiment of the invention, the confectionery product comprises less than 10% by weight of plasticizers, preferably less than 8% by weight of plasticizers and most preferably less than 4% by weight of plasticizers.

According to a preferred embodiment of the invention, a relatively low amount of plasticizers should be applied in order to obtain the desired textural properties, i.e. the toffee-like chew feel. Moreover, off-notes may be present if too much plasticizer is present, especially when applying triacetin and glycerides. Finally, plasticizers such as triacetin and acetylated glycerides are expensive and the amount should be kept low.

In an embodiment of the invention, said plasticizer comprises triacetin.

In an embodiment of the invention, said plasticizer comprises acetylated glycerides.

In an embodiment of the invention, said confectionery product comprises a polymer system in an amount of from about 5% to about 99% by weight, flavor in an amount of about 0.001% to about 30% by weight and sweeteners in an amount of about 5% to about 80% by weight.

Flavors, sweeteners and further ingredients may be selected from those mentioned in the detailed description of the present invention.

In an embodiment of the invention, said confectionery product comprises a polymer system in an amount of from about 10% to about 99% by weight of said confectionery product.

In an embodiment of the invention, said confectionery product comprises a polymer system in an amount of from about 20% to about 99% by weight of said confectionery product.

In an embodiment of the invention, said confectionery product comprises a polymer system in an amount of from about 30% to about 99% by weight of said confectionery product.

The quantity of polymer system in a toffee gum, according to the invention, may be regulated in order to obtain a certain desired balance between substance retained in the mouth when consuming the product and substance being swallowed by the user.

The applied amount of polymer system furthermore affects the consistency of the product in combination with further ingredients such as softeners, sweeteners and flavors.

According to the most preferred embodiment of the invention, the amount of polymer system is regulated within the range of 30 to 65 weight percent of the toffee gum. If the percentage of polymer system gets too low, it may cause difficulty with the coherence and shape of the product. On the other hand, if the percentage of polymer system is too high, it may cause the product to be less tasty and more tiring to consume and chew.

In an embodiment of the invention, said confectionery product comprises a chewable tablet comprising a chewable polymer system.

According to the invention, the confectionery product may be evaluated to have advantageous textural properties comparable to toffee. Such hybrid confectionery product may thus be dimensioned to be a hybrid toffee chewing gum product. The toffee texture of the polymer based confectionery product according to the invention is obtained through a substantial amount of polyvinyl acetate and avoiding use of substantial amounts of high-molecular weight polymers, in particular elastomers.

In an embodiment of the invention, said flavor comprises substantially oil-based and/or substantially hydrophilic flavors.

According to an embodiment of the invention, substantially oil-based flavors are preferred as such flavors tend to match the polymer system, which according to the invention may be regarded hydrophilic.

According to a further embodiment of the invention, substantially hydrophilic flavors have proved advantageous e.g. with respect to prolongation of release.

In an embodiment of the invention, said confectionery product may be formed in different shapes such as cores, ellipsoid, balls, cylinders, squares, rectangular, hexagonal, strips, paraboloid, donut formed, ring formed, teddy bear formed and/or multi-modular.

In an embodiment of the invention, the weight of the confectionery product is from about ¼ gram to about 10 grams, preferably from about ½ gram to about 5 grams.

In an embodiment of the invention, the confectionery product comprises a coating.

The confectionery product according to the invention is suitable for almost any coating method within the art, such as hard coating, film coating, soft coating, etc.

In a further advantageous embodiment of the invention, several layers of coatings may be applied and the layers may comprise or be formed by different types of layer substance.

In an advantageous embodiment of the invention, chocolate may be applied as a coating, a product module or center filling as the polymer system has proved robust to such quite aggressive plasticizing component, which typically tends to dissolve conventional chewing gum formulations.

In accordance with the invention, the confectionery product comprises about 0% to about 75% by weight of an outer coating applied onto the confectionery product center. Suitable coating types include hard coatings, film coatings and soft coatings of any composition including those currently used in coating of chewing gum, pharmaceutical products and confectioneries.

According to a preferred embodiment of the invention, film coating is applied to the confectionery product.

One presently preferred outer coating type is a hard coating, which term is used in the conventional meaning of that term including sugar coatings and sugar-free (or sugarless) coatings and combinations thereof. The object of hard coating is to obtain a sweet, crunchy layer which is appreciated by the consumer and to protect the confectionery product centers for various reasons. In a typical process of providing the confectionery product centers with a protective sugar coating the confectionery product centers are successively treated in suitable coating equipment with aqueous solutions of crystallizable sugar such as sucrose or dextrose, which, depending on the stage of coating reached, may contain other functional ingredients, e.g. fillers, colors, etc. In the present context, the sugar coating may contain further functional or active compounds including flavor compounds, pharmaceutically active compounds and/or polymer degrading substances.

In the production of confectionery product it may, however, be preferred to replace the cariogenic sugar compounds in the coating by other, preferably crystallizable, sweetening compounds that do not have a cariogenic effect. In the art such coatings are generally referred to as sugarless or sugar-free coatings. Presently preferred non-cariogenic hard-coating substances include polyols, e.g. sorbitol, maltitol, mannitol, xylitol, erythritol, lactitol, isomalt and tagatose which are obtained by industrial methods by hydrogenation of D-glucose, maltose, fructose or levulose, xylose, erythrose, lactose, isomaltulose and D-galactose, respectively.

In a typical hard-coating process, as it will be described in details in the following, syrup containing crystallizable sugar and/or polyol is applied onto the confectionery product centers and the water it contains is evaporated off by blowing with warm, dry air. This cycle must be repeated several times, typically 10 to 80 times, in order to reach the swelling required. The term "swelling" refers to the increase in weight of the products, as considered at the end of the coating operation by comparison with the beginning, and in relation to the final weight of the coated products. In accordance with the present invention, the coating layer constitutes for example about 0% to 75% by weight of the finished confectionery product, such as about 10% to 60% by weight, including about 15% to 50% by weight.

In further useful embodiments, the outer coating of the confectionery product element of the invention is subjected to a film-coating process and which therefore comprises one or more film-forming polymeric agents and optionally one or more auxiliary compounds, e.g. plasticizers, pigments and opacifiers. A film coating is a thin polymer-based coating applied to a confectionery product center of any of the above forms. The thickness of such a coating is usually between 20 and 100 μm. Generally, the film coating is obtained by passing the confectionery product centers through a spray zone with atomized droplets of the coating materials in a suitable aqueous or organic solvent vehicle, after which the material adhering to the confectionery product centers is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers also referred to as functional polymers are polymers that, in addition to its film-forming characteristics, confer a modified release performance with respect to active components of the confectionery product formulation. Such release-modifying polymers include methylacrylate ester copolymers, ethylcellulose (EC) and enteric polymers designed to resist the acidic stomach environment, yet dissolve readily in the duodenum. The latter group of polymers includes: cellulose acetate phthalate (CAP), polyvinyl acetate phthalate (PVAP), shellac, methacrylic acid copolymers, cellulose acetate trimellitate (CAT) and HPMC. It will be appreciated that the outer film coating according to the present invention may comprise any combination of the above film-coating polymers.

In other embodiments, the film-coating layer of the confectionery product elements, according to the invention, comprises a plasticizing agent having the capacity to alter the physical properties of a polymer to render it more useful in performing its function as a film-forming material. In general, the effect of plasticizers will be to make the polymer softer and more pliable as the plasticizer molecules interpose themselves between the individual polymer strands thus breaking down polymer-polymer interactions. Most plasticizers used in film coating are either amorphous or have very little crystallinity. In the present context, suitable plasticizers include polyols such as glycerol, propylene glycol, polyethylene glycol, e.g. the 200-6,000 grades thereof, organic esters such as phthalate esters, dibutyl sebacate, citrate esters and triacetin, oils/glycerides including castor oil, acetylated monoglycerides and fractionated coconut oil.

The choice of film-forming polymer(s) and plasticizing agent(s) for an optional outer coating of the present confectionery product is made with due consideration for achieving the best possible barrier properties of the coating in respect of dissolution and diffusion across the film of moisture and gasses.

The film coating of the confectionery product elements may also contain one or more colorants or opacifiers. In addition to providing a desired color, such agents may contribute to protecting the confectionery product against pre-chewing reactions, in particular by forming a barrier against moisture and gasses. Suitable colorants/pacifiers include organic dyes and their lakes, inorganic coloring agents, e.g. titanium oxide and natural colors such as e.g. β-carotene.

Additionally, film coatings may contain one or several auxiliary substances such as flavors and waxes or saccharide compounds such as polydextrose, dextrins including maltodextrin, lactose, modified starch, a protein such as gelatine or zein, a vegetable gum and any combination thereof.

It is also an aspect of the present invention that the outer coating of the confectionery product can contain one or more pharmaceutical or cosmetical components including those mentioned hereinbefore.

Accordingly, in further embodiments, an above hard-coated or film-coated confectionery product element of the invention is an element where the outer coating comprises at least one additive component selected from a binding agent, a moisture-absorbing component, a film-forming agent, a dispersing agent, an antisticking component, a bulking agent, a flavoring agent, a coloring agent, a pharmaceutically or cosmetically active component, a lipid component, a wax component, a sugar, and an acid. If it is desired to defer the effect of any of these additive components in the outer coating until mastication of the confectionery product, such components may, in accordance with the invention be encapsulated using any conventional encapsulation agent such as e.g. a protein including gelatine and soy protein, a cellulose derivative including any of those mentioned above, a starch derivative, edible synthetic polymers and lipid substances, the latter optionally in the form of liposome encapsulation.

In other embodiments, the confectionery product element according to the invention is provided with an outer coating in the form generally described in the art as a soft coating. Such soft coatings are applied using conventional methods and may advantageously consist of a mixture of a sugar or any of the above non-cariogenic, sugar-less sweetening compounds, and a starch hydrolysate.

Again, it should be noted that the above-described coating is optional or that it may be postponed until it fits into the last part of the manufacturing process due to the fact that the applied barrier layer is also acting as a complete or at least a partial barrier to transfer of humidity from the environment into the tablet.

In an embodiment of the invention, the confectionery product is center filled.

In an embodiment of the invention, the confectionery product comprises active ingredients.

Examples of suitable active ingredients are listed below.

In one embodiment the confectionery product according to the invention comprises a pharmaceutically, cosmetically or biologically active substance. Examples of such active substances, a comprehensive list of which is found e.g. in WO 00/25598, which is incorporated herein by reference, include drugs, dietary supplements, antiseptic agents, pH adjusting agents, anti-smoking agents and substances for the care or treatment of the oral cavity and the teeth such as hydrogen peroxide and compounds capable of releasing urea during chewing. Examples of useful active substances in the form of antiseptics include salts and derivatives of guanidine and bisguanidine (for instance chlorhexidine diacetate) and the following types of substances with limited water-solubility: quaternary ammonium compounds (e.g. ceramine, chloroxylenol, crystal violet, chloramine), aldehydes (e.g. paraformaldehyde), derivatives of dequaline, polynoxyline, phenols (e.g. thymol, p-chlorophenol, cresol), hexachlorophene, salicylic anilide compounds, triclosan, halogens (iodine, iodophores, chloroamine, dichlorocyanuric acid salts), alcohols (3,4 dichlorobenzyl alcohol, benzyl alcohol, phenoxyethanol, phenylethanol), cf. also Martindale, The Extra Pharmacopoeia, 28th edition, pages 547-578; metal salts, complexes and compounds with limited water-solubility, such as aluminum salts, (for instance aluminum potassium sulphate $AlK(SO_4)_2,12H_2O$) and salts, complexes and compounds of boron, barium, strontium, iron, calcium, zinc, (zinc acetate, zinc chloride, zinc gluconate), copper (copper chloride, copper sulphate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium. Further active substances can be found in J. Dent. Res. Vol. 28 No. 2, pages 160-171, 1949.

Examples of active substances in the form of agents adjusting the pH in the oral cavity include: acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

Active ingredients may comprise the below-mentioned compounds or derivates thereof but are not limited thereto: Acetaminophen, Acetyl salicylic acid, Buprenorphine Bromohexan Celecoxib Codeine, Diphenhydramine, Diclofenac, Etoricoxib, Ibuprofen, Indometacin, Ketoprofen, Lumiracoxib, Morphine, Naproxen, Oxycodone, Parecoxib, Piroxicam, Pseudoephedrine, Rofecoxib, Tenoxicam, Tramadol, Valdecoxib, Calcium carbonate, Magaldrate, Disulfiram, Bupropion, Nicotine, Azithromycin, Clarithromycin, Clotrimazole, Erythromycin, Tetracycline, Granisetron, Ondansetron, Promethazine, Tropisetron, Brompheniramine, Cetirizine, leco-Ceterizin, Chlorocyclizine, Chlorpheniramine, Chlorpheniramine, Difenhydramine, Doxylamine, Fenofenadin, Guaifenesin, Loratidine, desLoratidine, Phenyltoloxamine, Promethazine, Pyridamine, Terfenadine, Troxerutin, Methyldopa, Methylphenidate, Benzalcon, Chloride, Benzeth, Chloride, Cetylpyrid, Chloride, Chlorhexidine, Ecabet-sodium, Haloperidol, Allopurinol, Colchicine, Theophylline, Propranolol, Prednisolone, Prednisone, Fluoride, Urea, Actot, Glibenclamide, Glipizide, Metformin, Miglitol, Repaglinide, Rosiglitazone, Apomorphine, Cialis, Sildenafil, Vardenafil, Diphenoxylate, Simethicone, Cimetidine, Famotidine, Ranitidine, Ranitidine, cetirizine, Loratadine, Aspirin, Benzocaine, Dextromethorphan, Phenylpropanolamine, Pseudoephedrine, Cisapride, Domperidone, Metoclopramide, Acyclovir, Dioctylsulfosuccinic, Phenolphthalein, Almotriptan, Eletriptan, Ergotamine, Migea, Naratriptan, Rizatriptan, Sumatriptan, Zolmitriptan, Aluminum salts, Calcium salts, Ferro salts, Ag-salts, Zinc-salts, Amphotericin B, Chlorhexidine, Miconazole, Triamcinolonacetonid, Melatonin, Phenobarbital, Caffeine, Benzodiazepine, Hydroxyzine, Meprobamate, Phenothiazine, Buclizine, Brometazine, Cinnarizine, Cyclizine, Difenhydramine, Dimenhydrinate, Buflomedil, Amphetamine, Ephedrine, Orlistat, Phenylephedrine, Phenylpropanolamine, Pseudoephedrine, Sibutramine, Ketoconazole, Nitroglycerin, Nystatin, Progesterone, Testosterone, Vitamin B12, Vitamin C, Vitamin A, Vitamin D, Vitamin E, Pilocarpine, Aluminumaminoacetat, Cimetidine, Esomeprazole, Famotidine, Lansoprazole, Magnesium oxide, Nizatide and/or Ranitidine.

The invention is suitable for increased or accelerated release of active agents selected among the group of dietary supplements, oral and dental compositions, antiseptic agents, pH adjusting agents, anti-smoking agents, sweeteners, flavorings, aroma agents or drugs. Some of those will be described below.

The active agents to be used in connection with the present invention may be any substance desired to be released from the confectionery product. The active agents, for which a controlled and/or accelerated rate of release is desired, are primarily substances with a limited water-solubility, typically below 10 g/100 ml inclusive of substances which are totally water-insoluble. Examples are medicines, dietary supplements, oral compositions, anti-smoking agents, highly potent sweeteners, pH adjusting agents, flavorings, etc.

Other active ingredients are, for instance, paracetamol, benzocaine, cinnarizine, menthol, carvone, caffeine, chlorhexidine-di-acetate, cyclizine hydrochloride, 1,8-cineol, nandrolone, miconazole, mystatine, sodium fluoride, nicotine, cetylpyridinium chloride, other quaternary ammonium compounds, vitamin E, vitamin A, vitamin D, glibenclamide or derivatives thereof, progesterone, acetyl-salicylic acid, dimenhydrinate, cyclizine, metronidazole, sodium hydrogen carbonate, the active components from ginkgo, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, folic acid, niacin, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutritionists accepted by the authorities in different countries such as for instance US code of Federal Regulations, Title 21, Section 182.5013.182 5997 and 182.8013-182.8997.

Examples of active agents in the form of compounds for the care or treatment of the oral cavity and the teeth are for instance bound hydrogen peroxide and compounds capable of releasing urea during chewing.

Examples of active agents in the form of antiseptics are for instance salts and compounds of guanidine and bisguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogens (iodine, iodo-phores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulphate $AlK(SO_4)_2,12H_2O$) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, amino fluorides, stannous fluoride), phosphates, carbonates and selenium.

Cf. furthermore J. Dent. Res. Vol. 28 No. 2, pages 160-171, 1949, wherein a wide range of tested compounds is mentioned.

Examples of active agents in the form of agents adjusting the pH in the oral cavity include for instance: acceptable acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

In a further embodiment, the sucrose fatty acid esters may also be utilized for increased release of sweeteners including for instance the so-called highly potent sweeteners, such as for instance saccharin, cyclamate, aspartame, thaumatin, dihydrochalcone, stevioside, glycyrrhizin or salts or compounds thereof. For increased released of sweetener, the sucrose fatty acids preferable have a content of palmitate of at least 40% such as at least 50%.

Further examples of active agents are medicines of any type.

Examples of active agents in the form of medicines include caffeine, salicylic acid, salicylic amide and related substances (acetylsalicylic acid, choline salicylate, magnesium salicylate, sodium salicylate), paracetamol, salts of pentazocine (pentazocine hydrochloride and pentazocine-lactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedipine as well as suitable substances and salts thereof mentioned in Pharm. Int., November 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen®, Sildenafil citrate and derivatives thereof.

Dental products include Carbamide, CPP Casein Phospho Peptide; Chlorhexidine, Chlorhexidine di acetate, Chlorhexidine Chloride, Chlorhexidine di gluconate, Hexetidine, Strontium chloride, Potassium Chloride, Sodium bicarbonate, Sodium carbonate, Fluor containing ingredients, Fluorides, Sodium fluoride, Aluminum fluoride, Ammonium fluoride, Calcium fluoride, Stannous fluoride, Other fluor containing ingredients Ammonium fluorosilicate, Potassium fluorosilicate, Sodium fluorosilicate, Ammonium monofluorophosphate, Calcium monofluorophosphate, Potassium monofluorophosphate, Sodium monofluorophosphate, Octadecenyl Ammonium fluoride, Stearyl Trihydroxyethyl Propylenediamine Dihydrofluoride.

Vitamins include A, B1, B2, B6, B12, Folinic acid, Folic acid, niacin, Pantothenic acid, biotine, C, D, E, K. Minerals include Calcium, Phosphorus, Magnesium, Iron, Zinc, Copper, Iodine, Manganese, Chromium, Selenium, Molybdenum. Other active ingredients include: Q10® enzymes. Natural drugs including Ginkgo Biloba, ginger, and fish oil.

The invention also relates to use of migraine drugs such as Serotonin antagonists: Sumatriptan, Zolmitriptan, Naratriptan, Rizatriptan, Eletriptan; nausea drugs such as Cyclizine, Cinnarizine, Difenhydramine, Dimenhydrinate; hay fever drugs such as Cetirizine, Loratidine, pain relief drugs such as Buprenorphine, Tramadol, oral disease drugs such as Miconazole, Amphotericin B, Triamcinolonaceton;

and the drugs Cisapride, Domperidone, Metoclopramide. In a preferred embodiment, the invention relates to the release of Nicotine and its salts.

Moreover, the invention relates to a method of manufacturing a confectionery product according to the claims, whereby the product is manufactured by a batch process.

A well-known batch manufacturing method is a two-step process according to which the polymer system (within the terms of chewing gum referred to as the gum base) is mixed in a first step on the basis of substantially hydrophobic components and where upon the further hydrophilic components such as sweeteners, etc. are mixed together with the polymer system.

Moreover, the invention relates to a method of manufacturing a confectionery product according to the claims, whereby the product is manufactured by an extruder process.

Manufacturing of the confectionery product and/or the polymer system of the product may advantageously be performed by extruding. The process is very attractive and advantageous in relation to the present invention due to the fact that the polymer system (the gum base equivalent) comprises very few components, e.g. preferably three components: an LMw PVA, an HMw PVA, and a plasticizer, e.g. triacetin.

Moreover, the invention relates to, a method of manufacturing a confectionery product according to the claims, whereby the product is manufactured by a compression process.

According to an embodiment of the invention, it may be advantageous to apply compression techniques in the manufacture of the toffee gum. E.g. when incorporating ingredients being vulnerable to elevated temperatures or mixing processes, it may be preferable to apply compression in the preparation of the toffee gum of the present invention.

BRIEF DESCRIPTION OF THE DRAWINGS

The invention will be described with reference to the figures where.

DETAILED DESCRIPTION OF THE INVENTION

Figure 1:
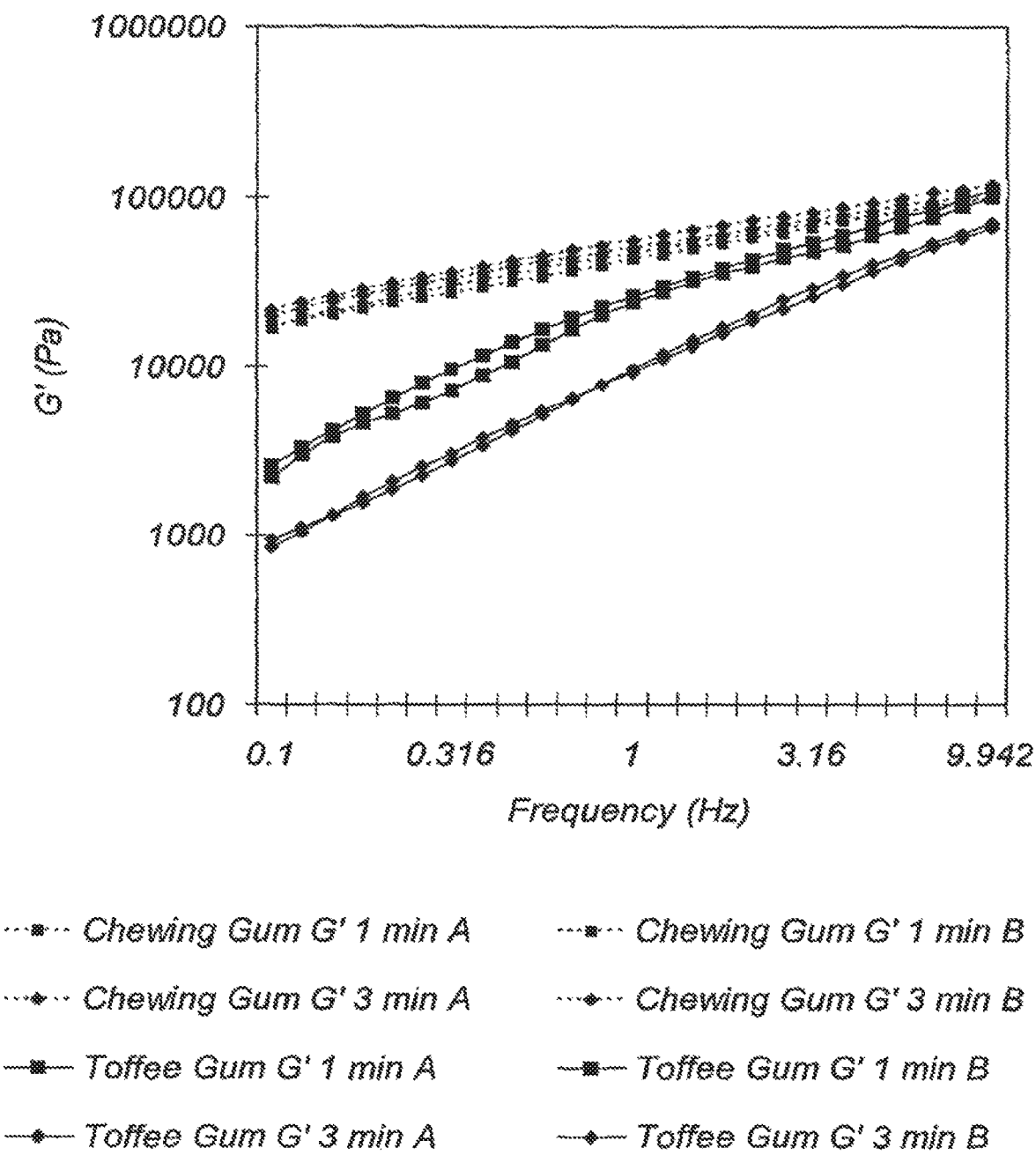
FIG. 1 illustrates a graph of the storage modulus G' as a function of chewing frequency.

According to the present invention, a confectionery product has been provided, which has striking resemblance with toffee-products, but which is based on a polymer system mainly composed of polyvinyl acetate. The polymer system is mixed with further ingredients, at least comprising sweetener and flavor, and the mixture forms a confectionery substance, which is herein referred to as a toffee gum substance. The confectionery product may also be referred to as a toffee gum.

Generally, according to a preferred embodiment of the invention, the provided toffee gum confectionery product typically comprises a polymer system and additional ingredients comprising flavoring agents, sweetening agents, texture-modifying agents, further optional ingredients and chocolate. Most part of the additional ingredients may typically be water-soluble. However, lipo-soluble ingredients may be fully applicable, such as for example flavoring oils.

The polymer system may include one or more polymers and may be mixed with a softening agent. The polymers are retained in the mouth and not swallowed during use, which has the advantageous effect of prolonging the toffee-like experience compared to conventional toffee products, which are normally completely swallowed.

Softening agents may be mixed into the polymers before addition of further ingredients, or mixed into the toffee gum composition at any time during the mixing procedure. In an embodiment of the invention, a part of the softening agents are added early in the process, e.g. added to the polymers alone, and further parts of the softening agents are added later on in the mixing process of the toffee gum.

Different kinds of softening agents may be useful for adjusting the texture of a specific polymer system. The exact composition of the polymer system and specific choice of additional ingredients, including softening, flavoring and sweetening agents, define the release properties of the toffee gum. The release rate of flavor and sweetener may be adjusted to be higher or lower during different phases of a chewing- and consuming-period of the toffee gum.

By addition of flavoring and sweetening agents into the toffee gum, any desired taste may be obtained, such as for example liquorice, chocolate, toffee, fruit, etc.

A way of characterizing the texture of the toffee gum is to measure the rheological properties, which involves the storage modulus G' and the loss modulus G" and the relation between the two at different frequencies. The term storage modulus G' may also be regarded as the elastic modulus, while the term loss modulus G" may be regarded as the viscous modulus. The ratio of G" to G', that is G"/G', is a measure of the relative importance of the viscous to elastic contributions for a material at a given frequency, and may be evaluated at a given oscillation torque and a given temperature.

The desired texture properties may be obtained by a proper combination of non-elastomers such as PVA and softeners.

In the following, the toffee gum composition is described in further details, and examples are given of applicable components in the polymer system and of the additional ingredients in toffee gum products according to the invention.

In general, a toffee gum product composition according to the present invention typically comprises a water-soluble bulk portion, flavoring agents, and a water-insoluble chewable portion mainly composed of the polymer system. The water-soluble portion dissipates with a portion of the flavoring agent over a period of time during chewing, while the polymer system portion is retained in the mouth throughout the chewing.

The polymer system provides the masticatory substance of the confectionery product according to the invention and greatly imparts the chew characteristics of the final toffee gum product. Furthermore, the polymer system affects the release profile of flavors, and sweeteners and plays a significant role in the final product with respect to both texture and taste. Some of the applied flavoring agents may have affinity for the polymer system and may be retained by the polymer system and hence be released over a prolonged time of chewing the toffee gum. Other flavoring agents may be readily released, and some may be released faster when emulsifiers are applied. Furthermore, emulsifiers may affect an improved stability towards humidity in the climate, as the emulsifiers may facilitate a lower hydration and thus a reduced tendency of the toffee gum to flow.

The water-insoluble portion of the toffee gum confectionery product contains the polymer system and typically a small amount of further ingredients such as plasticizers, waxes, softeners, fillers, colorants and antioxidants.

Preferably, the polymer system may comprise about 15% to about 95% by weight of the toffee gum confectionery product, more typically in the range of about 30% to about 65% by weight of the toffee gum.

The composition of the polymer system may vary depending on the particular product to be prepared and on the desired masticatory and other sensory characteristics of the final product. However, according to the invention, it has been found that polyvinyl acetate has properties, which are essential in obtaining a toffee-like texture of the confectionery product, and according to the invention polyvinyl acetate should always constitute the main part of the applied polymer system.

The polymer system may comprise polyvinyl acetate in an amount of 70% to 100% by weight of the polymer system. The polymer system may preferably be composed mostly of relatively low-molecular weight polyvinyl acetate, which may sometimes be referred to as resinous polymers. Elastomers and high-molecular weight polyvinyl acetate can only be applied to a very limited degree without compromising the desired toffee-like texture.

Softening agents may be incorporated into the polymer system to modify the texture. Softening agents may be added in an amount of 0% to 30% by weight in relation to the polymer system. Mild softening ingredients of the toffee gum such as polyol syrup, e.g. maltitol syrup, may within a most suitable range be added to the toffee gum in an amount of about 0% to 25% by weight of the final toffee gum substance.

The polymer system may further be mixed with fillers, waxes and fats, but these components are generally not contributing to the desired toffee-like texture properties.

According to an embodiment of the invention, the polyvinyl acetate, which comprises 70% to 100% by weight of the polymer system, may have relatively low molecular weight (Mw). The low-molecular weight polyvinyl acetates, which, according to an embodiment of the invention, may be characterized as resinous, resin-like and non-elastomeric, may preferably have molecular weights (Mw) within the range of 1,000 to 250,000 g/mol, preferably 2,000 to 200,000 g/mol, and more preferably 4,000 to 100,000 g/mol. The polyvinyl acetate polymers may affect the firmness of the polymer system and toffee gum.

Unless otherwise indicated, as used herein with regard to polymers, the term "molecular weight" means weight average molecular weight (Mw) in g/mol.

Polyvinyl acetates of different molecular weights and the glass transition temperatures may be combined in the polymer system and by their individual properties, the firmness, softness and further textural properties of the toffee gum may be varied.

High-molecular weight polyvinyl acetates of molecular weight (Mw) in the range of 25,000 to 300,000 g/mol, more commonly 30,000 to 80,000 g/mol may comprise up to 30%, preferably not more than 20%, and most preferably below 10% by weight of the polymer system. The higher the molecular weight, the less amount may be applied without spoiling the desired toffee-like properties of the toffee gum product according to the invention.

In accordance with the general principles in manufacturing a toffee gum product within the scope of the invention, variations of different suitable ingredients are listed and explained below.

Colorants, whiteners and antioxidants are optional ingredients, which may be mixed with the polymer system and may comprise an amount of up to about 5% by weight of the polymer system. The antioxidants may e.g. be chosen among butylated hydroxytoluene (BHT), butyl hydroxyanisol (BHA), propylgallate and tocopherols, and preservatives. The coloring agents and whiteners may for example comprise FD&C-type dyes and lakes, fruit or vegetable extracts, titanium dioxide, and combinations thereof.

In an embodiment of the invention, the toffee gum may comprise one or more softening agents in an amount of about 0% to about 18% by weight of the toffee gum, more typically about 0% to about 12% by weight of the toffee gum.

The softeners as well as emulsifiers may, according to an embodiment of the invention, be added both during mixing of the polymer system and later during mixing of the final toffee gum.

The softening ingredient may soften the polymer system and toffee gum formulation and may contribute to encompass ingredients such as waxes, fats, oils, emulsifiers, surfactants and solubilizers, which may optionally be added.

The softening agents e.g. sucrose esters may include those disclosed in WO 00/25598, which is incorporated herein by reference. Softening agents may further include tallow, hydrogenated tallow, hydrogenated and partially hydrogenated vegetable oils, cocoa butter, degreased cocoa powder, glycerol monostearate, glyceryl triacetate, lecithin, mono-, di- and triglycerides, acetylated monoglycerides, fatty acids (e.g. stearic, palmitic, oleic and linoleic acids) and combinations thereof. According to an embodiment of the invention, the preferred softener applied in the toffee gum may be triacetin.

Addition of one or more emulsifiers, which are also supplying softness to the product, may furthermore contribute to providing the product with water-binding properties and a pleasant smooth surface, and to reduce potential adhesive properties of the product. In an embodiment of the invention, the emulsifiers may comprise 0% to 18% by weight, preferably 0% to 12% by weight of the polymer system. Examples of emulsifiers may include mono- and diglycerides of edible fatty acids, lactic acid esters and acetic acid esters of mono- and diglycerides of edible fatty acids, acetylated mono and diglycerides, sugar esters of edible fatty acids, Na—, K—, Mg—and Ca—stearates, lecithin, hydroxylated lecithin and the like.

In case of the presence of biologically or pharmaceutically active ingredients as defined below, certain specific emulsifiers and/or solubilizers may be added in the toffee gum formulation in order to disperse and release these ingredients.

In an embodiment of the invention, waxes and fats may be used for adjustment of consistency and for softening of the toffee gum confectionery product. In connection with the present invention, examples of waxes and fats include for instance rice bran wax, polyethylene wax, petroleum wax (refined paraffin and microcrystalline wax), paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

Above-mentioned fats are not preferred in large amounts in the toffee gum of the present invention, as they have a tendency to counteract the desired toffee-like texture of the product. However, chocolate components such as cocoa butter and cocoa powder are preferred ingredients according to the present invention, although they are usually not mixed into the toffee gum composition in large amounts.

If waxes and/or fats are mixed into the toffee gum, the amount should be at the most 30% by weight in relation to the polymer system. Keeping the amount of fat low in the toffee gum composition may have the advantageous effect that the toffee gum may be more robust for an inner filling of fatty ingredients such as chocolate and for a soft coating, e.g. a coating with chocolate.

In an embodiment of the invention, the toffee gum may surprisingly comprise filler in an amount of about 1% to 30%, preferably 2% to 15% by weight of the toffee gum. Examples of fillers and/or texturisers include magnesium and calcium carbonate, sodium sulphate, ground limestone, silicate compounds such as magnesium and aluminum silicate, kaolin and clay, aluminum oxide, silicon oxide, talc, titanium oxide, mono-, di- and tri-calcium phosphates, cellulose polymers, such as wood, and combinations thereof.

Additional ingredients, which may be added to the toffee gum composition, are flavoring agents, bulk sweeteners, high intensity sweeteners, acidulants, and other components that provide desired attributes.

Suitable bulk sweeteners include both sugar and non-sugar sweetening components. Bulk sweeteners typically constitute from about 2% to about 80% by weight of the toffee gum, more typically about 10% to about 75% by weight such as 20% to 70% by weight of the toffee gum.

Useful sugar sweeteners are saccharide-containing components including, but not limited to, sucrose, dextrose, maltose, dextrins, trehalose, D-tagatose, dried invert sugar, fructose, levulose, galactose, corn syrup solids, and the like, alone or in combination.

Sorbitol can be used as a non-sugar sweetener. Other useful non-sugar sweeteners include, but are not limited to, other sugar alcohols such as mannitol, xylitol, hydrogenated starch hydrolysates, maltitol, isomaltol, erythritol, lactitol and the like, alone or in combination.

High-intensity artificial sweetening agents can also be used alone or in combination with the above sweeteners. Preferred high-intensity sweeteners include, but are not limited to sucralose, aspartame, salts of acesulfame, alitame, neotame, twinsweet, saccharin and its salts, cyclamic acid and its salts, glycyrrhizin, dihydrochalcones, thaumatin, monellin, stevioside and the like, alone or in combination.

In order to provide longer lasting sweetness and flavor perception, it may be desirable to encapsulate or otherwise control the release of at least a portion of the artificial sweetener. Techniques such as wet granulation, wax granulation, spray drying, spray chilling, fluid bed coating, coacervation, encapsulation in yeast cells and fiber extrusion may be used to achieve the desired release characteristics. Encapsulation of sweetening agents can also be provided using another component, which is already generally applied in the toffee gum such as a resinous compound.

Usage level of the high-intensity artificial sweetener will vary considerably and will depend on factors such as potency of the sweetener, rate of release, desired sweetness of the product, level and type of flavor used and cost considerations. Thus, the active level of high-potency artificial sweetener may vary from about 0% to about 8% by weight, preferably 0.001% to about 5% by weight. When carriers used for encapsulation are included, the usage level of the encapsulated sweetener will be proportionately higher.

Combinations of sugar and/or non-sugar sweeteners can be used in the toffee gum formulation processed in accordance with the invention. Additionally, the softener may also provide additional sweetness such as aqueous sugar or alditol solutions.

If a low-calorie product is desired, a low-caloric bulking agent may be used. Examples of low-caloric bulking agents include polydextrose, Raftilose, Raftilin, fructooligosaccharides (NutraFlora®), palatinose oligosaccharides; guar gum hydrolysates (e.g. Sun Fiber®) or indigestible dextrins (e.g. Fibersol®). However, other low-caloric bulking agents may be used.

The toffee gum according to the present invention may contain aroma agents and flavoring agents including natural and synthetic flavorings e.g. in the form of natural vegetable components, essential oils, essences, extracts, powders, including acids and other substances capable of affecting the taste profile. Examples of liquid and powdered flavorings include coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

The toffee gum flavor may be a natural flavoring agent, which is freeze-dried, preferably in the form of a powder, slices or pieces or combinations thereof. The particle size may be less than 3 mm, less than 2-mm or more preferred less than 1 mm, calculated as the longest dimension of the particle. The natural flavoring agent may be in a form, where the particle size is from about 3 µm to 2 mm, such as from 4 µm to 1 mm. Preferred natural flavoring agents include seeds from fruit e.g. from strawberry, blackberry and raspberry.

Various synthetic flavors, such as mixed fruit flavors, may also be used in the composition of the toffee gum according to the invention. As indicated above, the aroma agent may be used in quantities smaller than those conventionally used. The aroma agents and/or flavors may be used in the amount from 0.01% to about 30% by weight of the final product depending on the desired intensity of the aroma and/or flavor used. Preferably, the content of aroma/flavor is in the range of 0.2% to 3% by weight of the total composition.

In an embodiment of the invention, the flavoring agents comprise natural and synthetic flavorings in the form of natural vegetable components, essential oils, essences, extracts, powders, including acids and other substances capable of affecting the taste profile.

Further toffee gum ingredients, which may be included in the toffee gum according to the present invention, include surfactants and/or solubilizers, especially when pharmaceutically or biologically active ingredients are present. As examples of types of surfactants to be used as solubilizers in a toffee gum composition according to the invention, reference is made to H. P. Fiedler, Lexikon der Hilfstoffe fur Pharmacie, Kosmetik and Angrenzende Gebiete, pages 63-64 (1981) and the lists of approved food emulsifiers of the individual countries. Anionic, cationic, amphoteric or non-ionic solubilizers can be used. Suitable solubilizers include lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene stearic acid esters.

Particularly suitable solubilizers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, block copolymers of ethylene oxide and propyleneoxide and polyoxyethylene fatty alcohol ether. The solubilizer may either be a single compound or a combination of several compounds. In the presence of an active ingredient, the toffee gum may preferably also comprise a carrier known in the arts of chewing gum and pharmaceutical ingredients.

Emulsifiers, which are used as softeners may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof.

According to an embodiment of the invention, the toffee gum may comprise a pharmaceutically, cosmetically or biologically active substance. Examples of such active substances, a comprehensive list of which is found e.g. in WO 00/25598, which is incorporated herein by reference.

The active agents to be used in connection with the present invention may be any substance desired to be released from the toffee gum. If an accelerated rate of release is desired, corresponding to the effect obtained for the flavor, the primary substances are those with limited water solubility, typically below 10 g/100 ml including substances which are entirely water insoluble. Examples are medicines, dietary supplements, oral compositions, anti-smoking agents, highly potent sweeteners, pH adjusting agents, etc.

Further examples of active ingredients include paracetamol, benzocaine, cinnarizine, menthol, carvone, caffeine, chlorhexidine-di-acetate, cyclizine hydrochloride, 1,8-cineol, nandrolone, miconazole, mystatine, aspartame, sodium fluoride, nicotine, saccharin, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogen carbonate, the active components from *ginkgo*, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, niacin, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutrients accepted by the authorities in different countries such as for instance US code of Federal Regulations, Title 21, Section 182.5013.182 5997 and 182.8013-182.8997.

Examples of active agents in the form of compounds for the care or treatment of the oral cavity and the teeth are for instance bound hydrogen peroxide and compounds capable of releasing urea during chewing.

Examples of active agents in the form of antiseptics are for instance salts and compounds of guanidine and bisguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogens (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulfate $AlK(SO_4)_2$, $12H_2O$) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium.

Cf. furthermore J. Dent. Res. Vol. 28 No. 2, page 160-171, 1949, wherein a wide range of tested compounds are mentioned.

Examples of active agents in the form of agents adjusting the pH in the oral cavity include for instance: acceptable acids, such as adipinic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

Further examples of active agents are medicines of any type.

Examples of active agents in the form of medicines include caffeine, salicylic acid, salicylic amide and related substances (acetylsalicylic acid, choline salicylate, magnesium salicylate, sodium salicylate), paracetamol, salts of pentazocine (pentazocine hydrochloride and pentazocine-lactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedipine as well as suitable substances and salts thereof mentioned in Pharm. Int., November 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin and heparin.

Other active ingredients include beta-lupeol, Letigen, Sildenafil citrate and derivatives thereof.

Dental products include Carbami, CPP Casein Phospho Peptide; Chlorhexidine, Chlorhexidine di acetate, Chlorhexidine Chloride, Chlorhexidine di gluconate, Hexetidine, Strontium chloride, Potassium Chloride, Sodium bicarbonate, Sodium carbonate, Fluor containing ingredients, Fluorides, Sodium fluoride, Aluminum fluoride, Ammonium fluoride, Calcium fluoride, Stannous fluoride, Other fluor containing ingredients, Ammonium fluorosilicate, Potassium fluorosilicate, Sodium fluorosilicate, Ammonium monofluorophosphate, Calcium monofluorphosphate, Potassium monofluorphosphate, Sodium monofluorphosphate, Octadecenyl Ammonium fluoride, Stearyl Trihydroxyethyl Propylenediamine Dihydrofluoride, Vitamins include A, B1, B2, B6, B12, Folinic acid, niacin, Pantothenamide, biotine, C, D, E, K.

Minerals include Calcium, Phosphorus, Magnesium, Iron, Zinc, Copper, Led, Manganese, Chromium, Selenium and Molybdenum. Other active ingredients include: Q10®, enzymes. Natural drugs including *Ginkgo Biloba*, ginger, and fish oil. The invention also relates to use of migraine drugs such as Serotonin antagonists: Sumatriptan, Zolmitriptan, Naratriptan, Rizatriptan, Eletriptan; nausea drugs such as Cyclizine, Cinnarizine, Difenhydramine, Difenhydrinate; hay fever drugs such as Cetirizine, Loratidine, pain relief drugs such as Buprenorphine, Tramadol, oral disease drugs such as Miconazole, Amphotericin B, Triamcinolonaceton; and the drugs Cisapride, Domperidone, Metoclopramide.

Active ingredients may comprise the below-mentioned compounds or derivates thereof but are not limited thereto: Acetaminophen, Acetyl salicylic acid, Buprenorphine, Bromohexan, Celecoxib, Codeine, Diphenhydramine, Diclofenac, Etoricoxib, Ibuprofen, Indometacin, Ketoprofen, Lumiracoxib, Morphine, Naproxen, Oxycodone, Parecoxib, Piroxicam, Pseudoephedrine, Rofecoxib, Tenoxicam, Tramadol, Valdecoxib, Calcium carbonate, Magaldrate, Disulfiram, Bupropion, Nicotine, Azithromycin, Clarithromycin, Clotrimazole, Erythromycin, Tetracycline, Granisetron, Ondansetron, Promethazine, Tropisetron, Brompheniramine, Cetirizine, leco-Ceterizin, Chlorocyclizine, Chlorpheniramine, Chlorpheniramine, Difenhydramine, Doxylamine, Fenofenadin, Guaifenesin, Loratidine, desLoratidine, Phenyltoloxamine, Promethazine, Pyridamine, Terfenadine, Troxerutin, Methyldopa, Methylphenidate, Benzalcon, Chloride, Benzeth, Chloride, Cetylpyrid, Chloride, Chlorhexidine, Ecabet-sodium, Haloperidol, Allopurinol, Colchicine, Theophylline, Propranolol, Prednisolone, Prednisone, Fluoride, Urea, Miconazole, Actot, Glibenclamide, Glipizide, Metformin, Miglitol, Repaglinide, Rosiglitazone, Apomorphine, Cialis, Sildenafil, Vardenafil, Diphenoxylate, Simethicone, Cimetidine, Famotidine, Ranitidine, Ranitidine, cetirizine, Loratadine, Aspirin, Benzocaine, Dextromethorphan, Ephedrine, Phenylpropanolamine, Pseudoephedrine, Cisapride, Domperidone, Metoclopramide, Acyclovir, Dioctylsulfosuccinic, Phenolphthalein, Almotriptan, Eletriptan, Ergotamine, Migea, Naratriptan, Rizatriptan, Sumatriptan, Zolmitriptan, Aluminum salts, Calcium salts, Ferro salts, Silver salts, Zinc-salts, Amphotericin B, Chlorhexidine, Miconazole, Triamcinolonacetonid, Melatonin, Phenobarbital, Caffeine, Benzodiazepine, Hydroxyzine, Meprobamate, Phenothiazine, Buclizine, Brometazine, Cinnarizine, Cyclizine, Difenhydramine, Dimenhydrinate, Buflomedil, Amphetamine, Ephedrine, Orlistat, Phenylephedrine, Phenylpropanolamine, Pseudoephedrine, Sibutramine, Ketoconazole, Nitroglycerin, Nystatin, Progesterone, Testosterone, Vitamin B12, Vitamin C, Vitamin A, Vitamin D, Vitamin E, Pilocarpine, Aluminumaminoacetat, Cimetidine, Esomeprazole, Famotidine, Lansoprazole, Magnesium oxide, Nizatide and/or Ranitidine.

In one embodiment of the invention, the flavor may be used as taste masking in a toffee gum comprising active ingredients, which themselves have undesired taste or which alter the taste of the formulation.

The toffee gum may optionally contain additives, such as binding agents, acidulants, fillers, coloring agents, preservatives, and antioxidants, for instance butylated hydroxytoluene (BHT), butyl hydroxyanisol (BHA), propylgallate and tocopherols.

Colorants and whiteners may include FD & C-type dyes and lakes, fruit and vegetable extracts, titanium dioxide, and combinations thereof.

Materials to be used for the above-mentioned encapsulation methods for sweeteners might e.g. include Gelatine, Wheat protein, Soya protein, Sodium caseinate, Casein, Gum arabic, Mod. starch, Hydrolyzed starches (maltodextrines), Alginates, Pectin, Carrageenan, Xanthan gum, Locus bean gum, Chitosan, Bees wax, Candelilla wax, Carnauba wax, Hydrogenated vegetable oils, Zein and/or Sucrose.

Generally, it is preferred that the polymer system of the toffee gum products prepared according to the invention is based mainly or solely on polyvinyl acetate.

However, within the scope of the invention, small amounts, never exceeding 30% by weight of the polymer system, of further natural or synthetic resins, and synthetic elastomers may be applied. Examples are mentioned below.

Examples of synthetic resins, which should be limited in amount, include vinyl acetate-vinyl laurate copolymers and terpene resins derived from alpha-pinene, beta-pinene, and/or d-limonene, and natural terpene resins. Examples of synthetic elastomers include those listed in Food and Drug Administration, CFR, Title 21, Section 172,615, the Masticatory Substances, Synthetic such as polyisobutylene. e.g. having a gel permeation chromatography (GPC) average molecular weight in the range of about 10,000 to 1,000,000 including the range of 50,000 to 80,000, isobutylene-isoprene copolymer (butyl elastomer), styrene-butadiene copolymers e.g. having styrene-butadiene ratios of about 1:3 to 3:1, polyisoprene, polyethylene, vinyl acetate-vinyl laurate copolymer e.g. having a vinyl laurate content of about 5% to 50% by weight such as 10% to 45% by weight of the copolymer, and combinations hereof.

High- and low-molecular weight synthetic elastomers may be combined in the same polymer system. Examples of such combinations are polyisobutylene and styrene-butadiene, polyisobutylene and polyisoprene, polyisobutylene and isobutylene-isoprene copolymer (butyl rubber) and a combination of polyisobutylene, styrene-butadiene copolymer and isobutylene isoprene copolymer.

Examples of natural resins are: Natural rosin esters, often referred to as ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins.

Although it is not preferred, it is within the scope of the invention to apply PVA, which comprises a limited amount of water, such as in the range of 0.1% to 4% by weight of the PVA.

Polymer systems of the invention are typically prepared by adding an amount of polyvinyl acetate, mostly low-molecular weight PVA, and plasticizer to a heated (10° C.-120° C.) sigma blade mixer with a front to rear speed ratio from about 1.2:1 to about 2:1, the higher ratio typically being used for a polymer system which requires more rigorous compounding of its medium/high-molecular weight polymers.

The initial amounts of ingredients comprising the initial mass may be determined by the working capacity of the mixing kettle in order to attain a proper consistency and by the degree of compounding desired to break down the although slight amount of medium/high-molecular weight polymers and increase chain branching. The longer the time of compounding, the use of lower molecular weight or softening point polymer system ingredients, the lower the viscosity and firmness of the final polymer system will be.

Compounding typically begins to be effective once the ingredients have massed together. Anywhere from 15 to 90 minutes may be the length of compounding time.

Preferably, the time of compounding is from 20 to about 60 minutes.

After the initial ingredients have massed homogeneously and compounded for the time desired, the balance of the polymer system ingredients are added in a sequential manner until a completely homogeneous molten mass is attained. Typically, any remainder of the polymer system components is added within 60 minutes after the initial compounding time.

Typical polymer system processing times may vary from about 0.5 to about 4 hours, preferably from about 0.5 to 1.5 hours, depending on the formulation. The final mass temperature when dumped may be between 70° C. and 130° C. and preferably between 100° C. and 120° C. The completed molten mass is emptied from the mixing kettle into coated or lined pans, extruded or cast into any desirable shape and allowed to cool and solidify. Those skilled in the art will recognize that many variations of the above-described procedure may be followed.

In general, a toffee gum product, according to the invention, may be manufactured by sequentially adding the various ingredients to a commercially available mixer. After the ingredients have been thoroughly mixed, the toffee gum mass is discharged from the mixer and shaped into the desired form such as by rolling into sheets and cutting into sticks, extruded into chunks or casting into pellets.

A typical example of the mixing procedure may in an embodiment of the invention involve the following. Generally, the ingredients may be mixed by first softening and mixing the polymer system. The softening agents or part of them may also be added at this time. Colors, active agents and/or emulsifiers may then be added, along with syrup and a portion of the bulking agent/sweetener. Further portions of the bulking agent/sweetener may then be added into the mixer. A flavoring agent may typically be added with the final portion of the bulking agent/sweetener. A high-intensity sweetener may preferably be added after the final portion of bulking agent.

The entire mixing procedure typically takes from 12 to 25 minutes, but longer mixing times may sometimes be required. Many variations of the above-described procedure may be followed, including a one-step method such as described in US patent application 2004/0115305, hereby incorporated as reference. Toffee gum products may be formed by extrusion, compression, rolling and may be center-filled with liquids and/or solids in any form.

According to a preferred embodiment of the invention, the toffee gum is manufactured by an extrusion process.

The following non-limiting examples illustrate the manufacturing of a toffee gum confectionery product according to the invention.

EXAMPLE 1

Preparation of Toffee Gins

Toffee gum products were prepared having the toffee gum substance formulations of table 1.

TABLE 1

Toffee gum compositions. Numbers are given in percentage by weight of the total composition. The applied polyvinyl acetate (PVA) of lower and higher molecular weight constituting 38.4% overall forms the polymer system

| Components | Toffee gum substance no. | |
| --- | --- | --- |
| | 101 | 102 |
| Polymer system component: PVA of Mw 10-20000 g/mol and $T_g$ of 33° C. | 38 | 38 |
| Polymer system component: PVA of Mw 40-60000 g/mol and $T_g$ of 37° C. | 0.4 | 0.4 |
| Softener | 4.6 | 2.1 |
| Sorbitol | 39.2 | 41.4 |
| Maltitol syrup | 10 | 8 |
| Xylitol | 6 | 6 |
| Flavor | 1.5 | 3.8 |
| Sweetener | 0.3 | 0.3 |

The preparation involved the following procedure: Polymer system and softeners were mixed in a mixer, such as e.g. a Z-blade mixing kettle. The mixing process was carried out at a temperature of about 40-80° C. for a period of about 10-25 minutes, thereby preparing a homogeneous mixture of each polymer system. In case, one single polymer constitutes the polymer system, the mixing procedure serves yet to modify the polymer texture prior to the application in a toffee gum according to the invention. The mixing process, the heating, and a possible softening agent all contribute to a softening of the polymer system prior to mixing of the final toffee gum substance composition.

The mixed polymer system may be discharged from the mixer and allowed to cool to room temperature before transferring into a second mixer. Alternatively, the mixed polymer system may be transferred in its heated state into a second mixer, or the polymer system may be kept within the first mixer ready for addition of the further ingredients to prepare the toffee gum.

The polymer system and the remainder components are all mixed together in a mixer at a temperature of about 40-80° C. A mixing kettle, e.g. with horizontally placed Z-shaped arms may for example be used. Initially, the polymer system and about half of the sorbitol powder are mixed for about 3 minutes. At this time, the mixer should preferably be at the required temperature of 40-80° C. If necessary, the mixer may be preheated, e.g. for about 15 minutes. After mixing the polymer system and the first half portion of the sorbitol, the remaining half portion of sorbitol is added and mixed for 2 minutes, whereupon maltitol syrup is slowly added and mixing is continued for 5 minutes. Flavors are then added, and the composition is mixed for 3 minutes. Softener is slowly added and mixed for about 2 minutes. Then high-intensity sweeteners are added and mixed for 3 minutes. Xylitol is added and mixing continued for 3 minutes, whereupon the resulting toffee gum composition is discharged and e.g. transferred to a pan at a temperature of 40-60° C. The product is then rolled and scored, punched or formed in another way into cores, sticks, balls, cubes, and any other desired shape, optionally followed by coating and polishing processes prior to packaging.

Evidently, within the scope of the invention, other processes and ingredients may be applied in the process of manufacturing the toffee gum.

EXAMPLE 2

A polymer system, according to an embodiment of the invention, is prepared by a method corresponding to the method typically applied for gum base mixing. The applied method involved mixing in a Z-blade mixer. The polymer system comprises the following components:
- 95% by weight of low-molecular weight PVA (15,000 g/mol Mw)
- 1% by weight of high-molecular weight PVA (60,000 g/mol Mw)
- 4% triacetin.

It should be noted that extruding of the polymer system may advantageously be applied within the scope of the invention.

EXAMPLE 3

A confectionery product is mixed on the basis of the polymer system of example 1. The mixing is performed by a method corresponding to the method typically applied for mixing of gum base together with the hydrophilic chewing gum components. The confectionery product comprised:
- 0.3% by weight of high intensity sweetener
- 39% by weight of bulk sweetener (xylitol and sorbitol)
- 6% by weight of maltitol syrup
- 1.5% by weight of acid
- 3.2% by weight of lemon flavor
- 50% by weight of the polymer system of example 1

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product.

EXAMPLE 4

A confectionery product is mixed on the basis of the polymer system of example 2. The mixing is performed by a method corresponding to the method typically applied for mixing of gum base together with the hydrophilic chewing gum components. The confectionery product comprised:
- 0.4% by weight of high intensity sweetener
- 3% by weight of triacetin
- 43.6% by weight of bulk sweetener (xylitol and sorbitol)
- 6% by weight of maltitol syrup
- 7% by weight of liquorice flavor
- 40% by weight of the polymer system of example 1

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product. It was furthermore observed that the confectionery product required a little more plasticizer compared to example 3. This is due to the fact that the lemon flavor and the associated acid tend to act as a significant supplementary plasticizer to the specifically applied triacetin.

EXAMPLE 5

A confectionery product is mixed on the basis of the polymer system of example 2. The mixing is performed by a method corresponding to the method typically applied for mixing of gum base together with the hydrophilic chewing gum components. The confectionery product comprised:
- 0.4% by weight of high intensity sweetener
- 3% by weight of triacetin
- 47.6% by weight of bulk sweetener (xylitol and sorbitol)
- 6% by weight of maltitol syrup
- 3% by weight of chocolate/hazelnut flavor
- 40% by weight of the polymer system of example 2

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product. Again, it was found advantageous to apply a little more plasticizer compared to example 3 for the same reasons as in example 4.

EXAMPLE 6

A confectionery product is mixed on the basis of the polymer system of example 2. The mixing is performed by a method corresponding to the method typically applied for mixing of gum base together with the hydrophilic chewing gum components. The confectionery product comprised:
- 0.4% by weight of high intensity sweetener
- 3% by weight of triacetin
- 47.6% by weight of bulk sweetener (xylitol and sorbitol)
- 6% by weight of maltitol syrup
- 3% by weight of mint flavor
- 40% by weight of the polymer system of example 2

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product. Again, it was found advantageous to apply a little more plasticizer compared to example 3 for the same reasons as in example 4.

EXAMPLE 7

The confectionery products of example 3-6 were coated by a hard coating comprising xylitol.

EXAMPLE 8

The confectionery products of example 5 and 6 were coated by a soft coating. The specifically applied soft coating is chocolate. It is noted that other soft coat materials may also be applied within the scope of the invention.

In an advantageous embodiment of the invention, chocolate may be applied as a coating, a product module or center filling as the polymer system has proved robust to such quite aggressive plasticizing component, which typically tends to dissolve conventional chewing gum formulations.

By evaluation it was noted that the desired toffee-character may be effectively supported and/or improved by the combination of toffee-like confectionery product according to the invention and chocolate.

Further layers of coatings may also be applied within the scope of the invention.

It is noted that the confectionery product may be manufactured in several different ways within the scope of the invention, including well-known two processes or e.g. by extruding.

It is moreover noted that the shape, size and weight may vary significantly according to the current desired properties of the product.

Various shapes may thus e.g. include round, ellipsoid, square, multimodular, ring-formed, etc.

One particular interesting variant is a center-filled confectionery structure. The polymer system applied, according to the invention, has thus proved quite resistant to e.g. fat-based ingredients such as chocolate prior to or subsequent to the chewing.

EXAMPLE 9

Comparison of Toffee Gum and Chewing Gum by Rheometric Measurements

Toffee gum cores were prepared from toffee gum substance no. 101 of example 1 and compared to chewing gum samples with regard to rheological properties and thus the texture. Measurements were carried out by an AR 1000 rheometer from TA Instruments and at an oscillation torque of 10 µN·m and 37° C.

Figure 2:
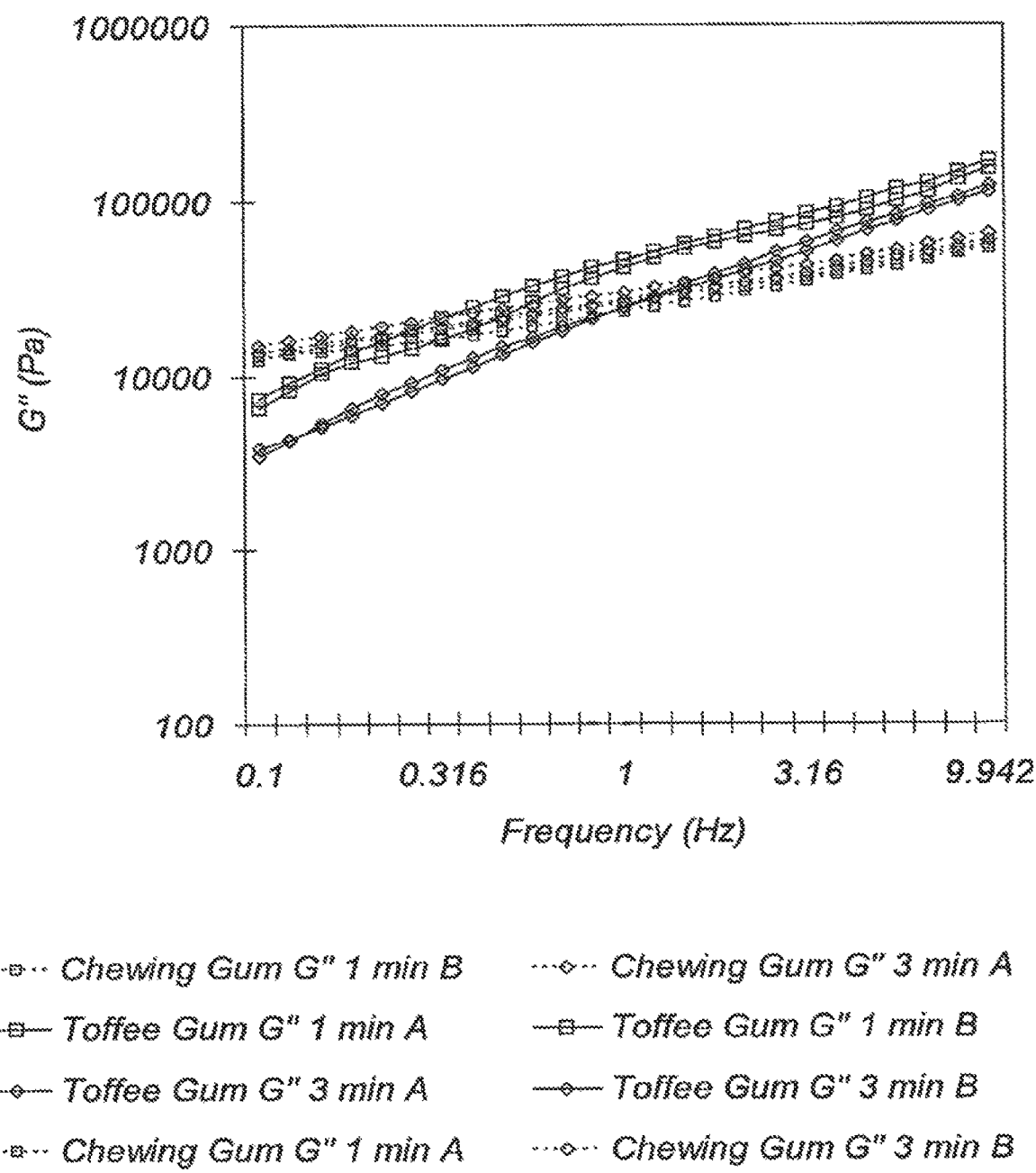
FIG. 2 illustrates a graph of the loss modulus G" as a function of chewing frequency.
Figure 3:
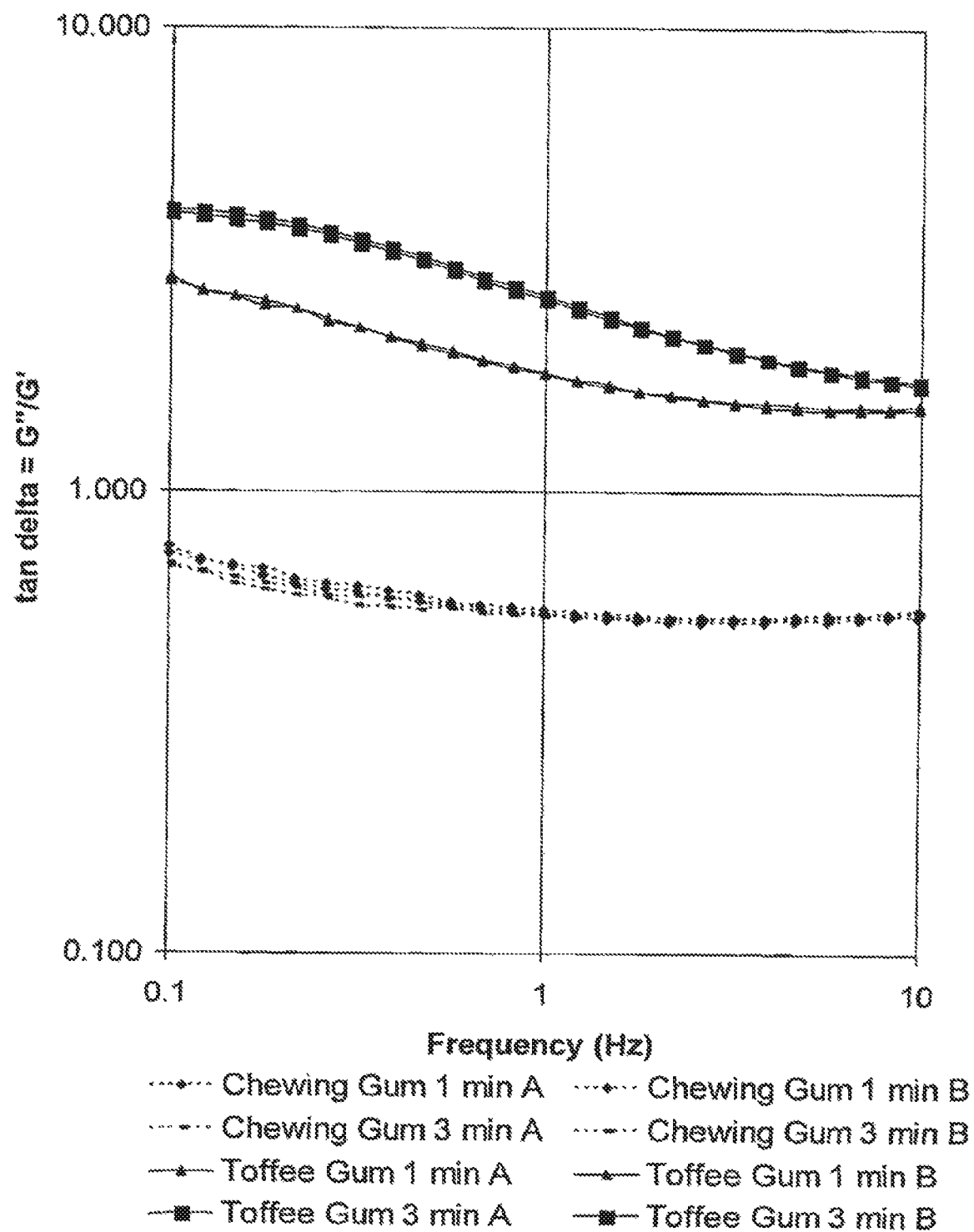
FIG. 3 illustrates tan (delta), the ratio between the storage modulus and the loss modulus G'/G", as a function of chewing frequency.

Results hereof are shown in FIGS. 1 to 3 depicting rheometric measurements of storage modulus G' (Pa), loss modulus G" (Pa) and Tan (delta) at increasing frequencies (Hz) for the tested samples of toffee gum and chewing gum. The tested samples included two samples of both toffee gum and chewing gum, which had been chewed for 1 minute, and likewise two samples of each product having been chewed for 3 minutes.

The conclusion when comparing toffee gum and chewing gum having been chewed for 1 minute are generally very similar to the conclusion of comparing samples having been chewed for 3 minutes.

A significant difference seen from the measurements is that for each sample of toffee gum, G" was larger than G', while the opposite relationship was found for chewing gum. This means that the toffee gum texture was dominated by G", i.e. the loss modulus, in contrast to chewing gum, which was dominated by G', i.e. the storage modulus. It is hereby evident that addition of elastomeric polymers, which increases the storage modulus, may destroy the desired toffee gum texture and cause a more chewing gum-like texture.

Looking at G' and G" independently, the following may be observed.

The slope of both G' and G" vs. frequency is clearly more steep in the measurements of toffee gum as compared to chewing gum.

At all the measured frequencies from 0.1 up to about 5 Hz, G' was clearly lower for the toffee gum samples than for the chewing gum samples. Thus, the storage modulus G' was less pronounced for toffee gum compared to chewing gum. Moreover, it is seen that at frequencies from about 2 Hz and more, G" was higher for the toffee gum samples than for the chewing gum samples. Thus, at these frequencies, the loss modulus G" was more pronounced for toffee gum compared to chewing gum.

It is furthermore noted that G' of the toffee gum samples were lower for samples having been chewed for 3 minutes than for the samples having only been chewed for 1 minute. The same is seen for G".

In contrast, the opposite is noticed for the chewing gum samples, for which G' and G" were on a higher level for the samples chewed for 3 minutes compared to only 1 minute.

Summing up, it has been found that the desired textural properties of the toffee gum may be attained, when one or more of the following properties are obtained:

the storage modulus G' is lower than the loss modulus G", the ratio of loss modulus G" to the storage modulus G' (i.e. G"/G or tan (delta)) is in the range of 1 to 10, the storage modulus G' decreases during at least a part of a chewing process, and/or the loss modulus G" decreases during at least a part of a chewing process.

EXAMPLE 10

Experiments were performed to investigate the influence on the rheological properties of the toffee gums by adding an amount of 5% by weight of filler; here talc and calcium carbonate. The measurements were performed after 1 min. of chewing at a chewing frequency of 1 Hz and a temperature of 37° C.

TABLE 2

|  | G' (Pa) | G" (Pa) | Tan(delta) |
| --- | --- | --- | --- |
| Talc 1 | 18,080 | 40,700 | 2,251 |
| Talc 2 | 20,130 | 44,960 | 2,233 |
| CaCO$_3$ 1 | 20,830 | 43,610 | 2,094 |
| CaCO$_3$ 2 | 21,990 | 45,670 | 2,077 |
| No filler 1 | 23,340 | 41,670 | 1,785 |
| No filler 2 | 25,680 | 46,310 | 1,803 |

A change was seen mainly in the storage modulus G' resulting in an increased tan (delta) indicating that the toffee properties are maintained when an amount of filler is included up to about 30% by weight of the final confectionery product.

What is claimed is:

1. A pharmaceutical tablet for use in administering one or more pharmaceutically active ingredients, comprising:
a polymer system;
the one or more pharmaceutically active ingredients;
the one or more pharmaceutically active ingredients including nicotine;
a flavor; and
a sweetener;
wherein at least 20% by weight of the pharmaceutical tablet comprises substantially non-elastomeric polymer and less than 5% by weight of the pharmaceutical tablet comprises one or a combination of elastomeric polymers; and
wherein the pharmaceutical tablet comprises polyvinyl acetate (PVA) in an amount of at least 70% by weight of said polymer system, wherein the pharmaceutical tablet comprises at least one low-molecular weight PVA having a molecular weight (Mw) of 2,000 to 40,000 g/mol in an amount of from 70 to 99% by weight of the polymer system,
wherein the polymer system comprises at least one high-molecular weight PVA having a Mw of 40,001 to 200,000 g/mol, and
wherein the pharmaceutical tablet comprises polymer having a Mw greater than 50,000 g/mol in an amount of less than 10% by weight of said polymer system.

2. The pharmaceutical tablet according to claim 1, wherein the pharmaceutical tablet comprises PVA in an amount of at least 90% by weight of said polymer system.

3. The pharmaceutical tablet according to claim 1, wherein the pharmaceutical tablet comprises PVA in an amount of at least 95% by weight of said polymer system.

4. The pharmaceutical tablet according to claim 1, wherein said polymer system comprises at least one substantially non-elastomeric polymer in an amount in the range of 80% to 100% by weight of said polymer system.

5. The pharmaceutical tablet according to claim 1, wherein the tablet comprises said polymer system in an amount of from 20% to 99% by weight of said tablet.

6. The pharmaceutical tablet according to claim 1, wherein the tablet comprises said polymer system in an amount of from 20% to 99% by weight of said tablet.

7. The pharmaceutical tablet according to claim 1, wherein the tablet comprises said polymer system in an amount of from 30% to 65% by weight of said tablet.

8. The pharmaceutical tablet according to claim 1, wherein the polymer system comprises vinyl acetate-vinyl laurate copolymer.

9. The pharmaceutical tablet according to claim 1, wherein the tablet is free of natural and synthetic elastomers.

10. The pharmaceutical tablet according to claim 1, wherein the tablet is free of natural resin and/or natural elastomers.

11. The pharmaceutical tablet according to claim 1, wherein the tablet comprises sweetener in an amount of 2% to 80% by weight.

* * * * *